US010328100B2

(12) United States Patent
Bentov et al.

(10) Patent No.: US 10,328,100 B2
(45) Date of Patent: *Jun. 25, 2019

(54) STABLE AMORPHOUS CALCIUM CARBONATE COMPRISING SYNTHETIC PHOSPHORYLATED PEPTIDES

(71) Applicant: Amorphical Ltd., Beer Sheva (IL)

(72) Inventors: Shmuel Bentov, M.P. Ha'ela (IL); Amir Sagi, Omer (IL); Amir Berman, Omer (IL); Assaf Shechter, Tel Aviv (IL)

(73) Assignee: AMORPHICAL LTD., Beer Sheva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/744,726

(22) Filed: Jun. 19, 2015

(65) Prior Publication Data

US 2016/0045546 A1    Feb. 18, 2016

Related U.S. Application Data

(60) Division of application No. 12/765,009, filed on Apr. 22, 2010, now abandoned, which is a continuation-in-part of application No. PCT/IL2008/001362, filed on Oct. 22, 2008.

(30) Foreign Application Priority Data

Oct. 22, 2007 (IL) .......................................... 186850
Aug. 14, 2008 (IL) .......................................... 193461

(51) Int. Cl.
| | |
|---|---|
| *A61K 9/00* | (2006.01) |
| *A61K 31/66* | (2006.01) |
| *A61K 33/10* | (2006.01) |
| *A61K 38/17* | (2006.01) |
| *C07K 14/435* | (2006.01) |

(52) U.S. Cl.
CPC ............ *A61K 33/10* (2013.01); *A61K 9/0053* (2013.01); *A61K 31/66* (2013.01); *A61K 38/17* (2013.01); *A61K 38/1767* (2013.01); *C07K 14/43509* (2013.01)

(58) Field of Classification Search
None
See application file for complete search history.

(56) References Cited

U.S. PATENT DOCUMENTS

| | | | |
|---|---|---|---|
| 4,237,147 | A | 12/1980 | Merten et al. |
| 4,964,894 | A | 10/1990 | Freepons |
| 6,265,200 | B1 | 7/2001 | De Leys et al. |
| 6,348,571 | B1 | 2/2002 | Redei et al. |
| 2007/0191963 | A1 | 8/2007 | Winterbottom et al. |
| 2008/0095819 | A1 | 4/2008 | Gourdie et al. |
| 2010/0310677 | A1 | 12/2010 | Bentov et al. |

FOREIGN PATENT DOCUMENTS

| | | | | |
|---|---|---|---|---|
| WO | 2005/115414 | A2 | 12/2005 | |
| WO | WO 2005115414 | A2 * | 12/2005 | ............. A61K 33/10 |
| WO | 2008/041236 | A2 | 4/2008 | |

OTHER PUBLICATIONS

Sugawara, Angewandte Chemie International Edition, 45, 18, 2006.*
Addadi et al., (2003) Taking advantage of disorder: amorphous calcium carbonate and its roles in biomineralization. Advanced Materials 15(12): 959-970.
Akiva-Tal et al., (2011) In situ molecular NMR picture of bioavailable calcium stabilized as amorphous CaCO3 biomineral in crayfish gastroliths. Proc Natl Acad Sci USA 108(36): 14763-14768.
Glimcher et al., (1984) Recent studies of the mineral phase in bone and its possible linkage to the organic matrix by protein-bound phosphate bonds. Philos Trans R Soc Lond B Biol Sci 304: 479-508.
Halloran and Donachy (1995) Characterization of organic matrix macromolecules from the shells of the Antarctic scallop, *Adamussium colbecki*. Comp Biochem Physiol B Biochem Mol Biol 111B(2): 221-231.
Hecker et al., (2003) Phosphorylation of serine residues is fundamental for the calcium-binding ability of Orchestin, a soluble matrix protein from crustacean calcium storage structures. FEBS Lett 535: 49-54.
Hu et al., (2010) Strongly bound citrate stabilizes the apatite nanocrystals in bone. Proc Natl Acad Sci USA 107(52): 22425-22429.
Inoue et al., (2001) Purification and structural determination of a phosphorylated peptide with anti-calcification and chitin-binding activities in the exoskeleton of the crayfish, *Procambarus clarkii*. Biosci Biotechnol Biochem 65(8): 1840-1848.
Inoue et al., (2007) Significance of the N- and C-terminal regions of CAP-1, a cuticle calcification-associated peptide from the exoskeleton of the crayfish, for calcification. Peptides 28: 566-573.
Johnsson et al., (1991) Adsorption and mineralization effects of citrate and phosphocitrate on hydroxyapatite. Calcif Tissue Int 49: 134-137.
Lee et al., (2005) Fabrication of unusually stable amorphous calcium carbonate in an ethanol medium. Materials Chemistry and Physics 93: 376-382.
Loste et al., (2003) The role of magnesium in stabilising amorphous calcium carbonate and controlling calcite morphologies. Journal of Crystal Growth 254: 206-218.
Luquet and Marin (2004) Biomineralisations in crustaceans: storage strategies. Comptes Rendus Palevol 3: 515-534.

(Continued)

*Primary Examiner* — Robert A Wax
*Assistant Examiner* — William Craigo
(74) *Attorney, Agent, or Firm* — Rothwell, Figg, Ernst & Manbeck, P.C.

(57) ABSTRACT

Provided are compositions containing amorphous calcium carbonate (ACC), and at least one phosphorylated peptide which stabilizes the amorphous form of said calcium carbonate. Particularly, the peptide can be selected from crustacean proteins, also provided by the invention, namely GAP65, GAP22, GAP21, and GAP12 (also indicated herein as GAP10). The compositions are useful in pharmaceutical and nutraceutical formulations.

11 Claims, 35 Drawing Sheets

Specification includes a Sequence Listing.

(56) References Cited

OTHER PUBLICATIONS

Ma et al., (2007) A novel extrapallial fluid protein controls the morphology of nacre lamellae in the pearl oyster, Pinctada fucata. J Biol Chem 282(32): 23253-23263.

Malkaj and Dalas (2007) The effect of acetaminophen on the crystal growth of calcium carbonate. J Mater Sci Mater Med 18: 871-875.

Manoli and Dalas (2002) The effect of sodium alginate on the crystal growth of calcium carbonate. J Mater Sci Mater Med 13: 155-158.

Martins et al., (2008) Hydroxyapatite micro- and nanoparticles: nucleation and growth mechanisms in the presence of citrate species. J Colloid Interface Sci 318: 210-216.

Maruyama et al., (2011) Synthesizing a composite material of amorphous calcium carbonate and aspartic acid. Materials Letters 65: 179-181.

Multigner et al., (1983) Pancreatic stone protein, a phosphoprotein which inhibits calcium carbonate precipitation from human pancreatic juice. Biochemical and Biophysical Research Communications 110(1): 69-74.

Reddi et al., (1980) Influence of phosphocitrate, a potent inhibitor of hydroxyapatite crystal growth, on mineralization of cartilage and bone. Biochem Biophys Res Commun 97(1): 154-159.

Rodriguez-Blanco et al., (2011) The role of pH and Mg on the stability and crystallization of amorphous calcium carbonate. Journal of Alloys and Compounds 536(Supp 1): S477-S479 International Symposium on Metastable, Amorphous and Nanostructured Materials, ISMANAM-2011 (Jun. 26 to Jul. 1, 2011).

Saitoh et al., (1985) Inhibition of calcium-carbonate precipitation by human salivary proline-rich phosphoproteins. Arch Oral Biol 30(8): 641-643.

Schneiders et al., (2007) Effect of modification of hydroxyapatite/ collagen composites with sodium citrate, phosphoserine, phosphoserine/ RGD-peptide and calcium carbonate on bone remodelling. Bone 40: 1048-1059.

Shechter et al., (2008) A gastrolith protein serving a dual role in the formation of an amorphous mineral containing extracellular matrix. Proc Natl Acad Sci U S A 105(20): 7129-7134.

Sugawara et al., (2006) Self-organization of oriented calcium carbonate/ polymer composites: Effects of a matrix peptide isolated from the exoskeleton of a crayfish. Angew Chem Int Ed Engl 45: 2876-2879.

Sugawara et al., (2006) 45(18): 2876-2879 Supporting information.

Thomas and Birchall (1983) The retarding action of sugars on cement hydration. Cement and Concrete Research 13: 830-842.

Tsutsui et al., (1999) Cloning and expression of a cDNA encoding an insoluble matrix protein in the gastroliths of a crayfish, Procambarus clarkia. Zoological Science (Tokyo) 16(4): 619-628.

Yudkovsky (2007) Hepatopancreatic multi-transcript expression patterns in the crayfish Cherax quadricarinatus during the moult cycle. Insect Molecular Biology 16(6): 661-674.

Internet site http://www.uniprot.org/uniprot/P98157.html—last modified Nov. 30, 2010—22 pages Database Uniprot P98157 (1996).

GenCore Database DQ847548, 2012.

* cited by examiner

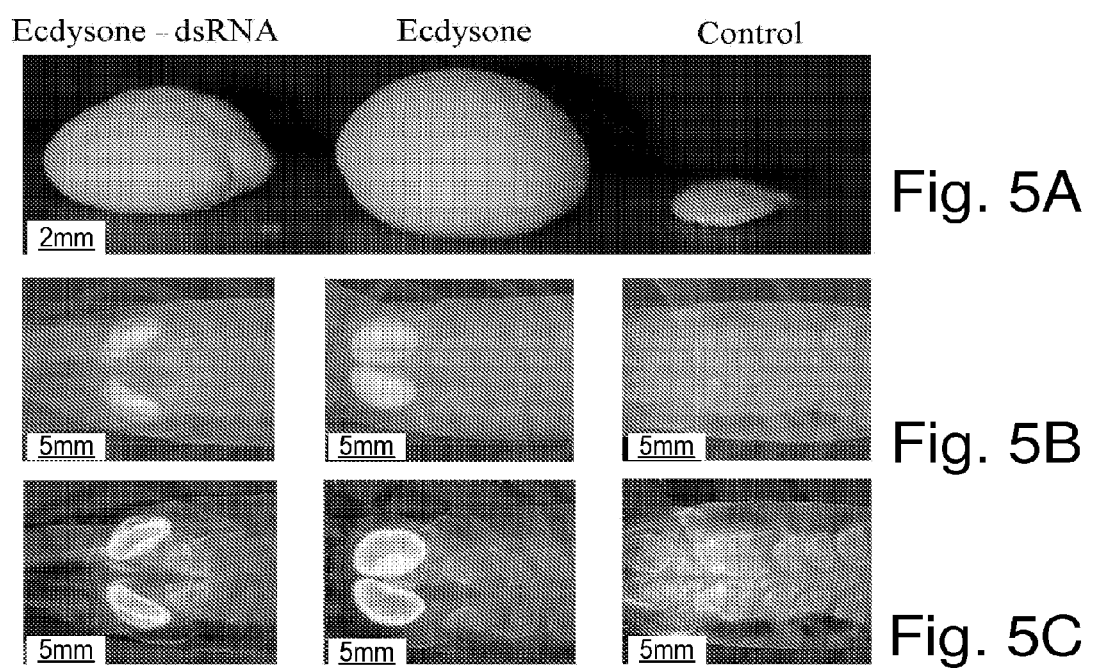

GASP 65   Trypsin
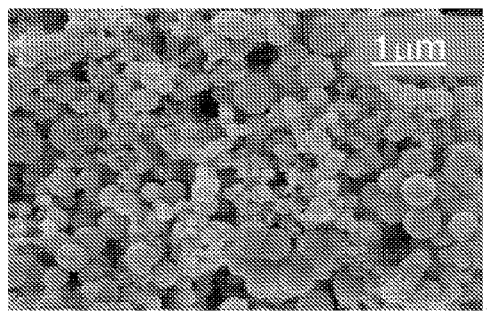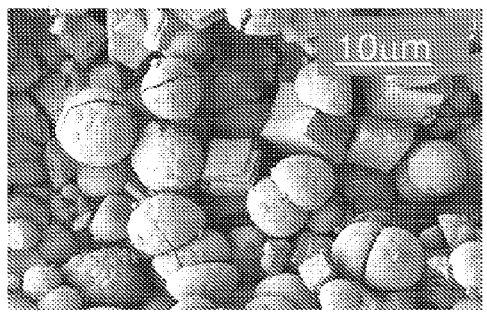
Fig. 7A
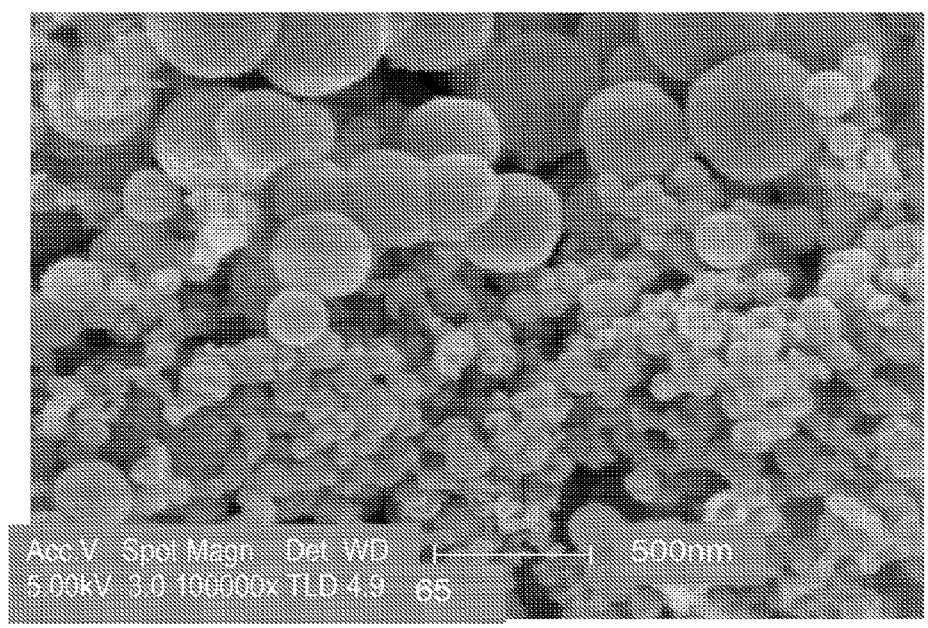
Fig. 7B

Table 1: Comparison of amino acid compositions of GAP proteins.

| | Amino acid | GAP 12 (9.9 kDa) pI-5.09 | GAP 21 (19.5 kDa) pI-4.8 | GAP 22 (28.6 kDa) pI-11.45 | GAP 65 (60.8 kDa) pI-5.01 |
|---|---|---|---|---|---|
| Non-polar Aliphatic | Glycine | 18.4% | 9.2% (17) | 5.6% (15) | 6.1% |
| | Alanine | 15.3% | 15.7% | 8.2% (22) | 4.7% |
| | Valine | 10.2% | 7.6% (14) | 4.5% (12) | 4.5% |
| | Leucine | 4.1% (4) | 8.6% (16) | 5.9% (16) | 5.1% |
| | Isoleucine | 0% (0) | 1.6% (3) | 4.8% (13) | 4.7% |
| | Methionine | 0% (0) | 0% (0) | 0% (0) | 2.8% |
| Aromatic | Phenylalanine | 5.1% (5) | 7% (13) | 1.1% (3) | 6.4% |
| | Tyrosine | 4.1% (4) | 0.5% (1) | 0.4% (1) | 3.0% |
| | Tryptophan | 2% (2) | 0% (0) | 0% (0) | 1.9% |
| Polar Uncharged | Serine | 4.1% (4) | 6.5% (12) | 6.7% (18) | 5.3% |
| | Proline | 8.2% (8) | 8.1% (15) | 25.7% | 6.8% |
| | Threonine | 3.1% (3) | 1.6% (3) | 8.2% (22) | 5.3% |
| | Cysteine | 0% (0) | 0% (0) | 0% (0) | 4.9% |
| | Aspargine | 8.2% (8) | 5.4% (10) | 0.7% (2) | 5.9% |
| | Glutamine | 4.1% (4) | 10.8% | 4.8% (13) | 5.3% |
| Positively charged | Lysine | 2% (2) | 0% (0) | 5.6% (15) | 4.0% |
| | Histidine | 1% (1) | 0.5% (1) | 1.9% (5) | 2.1% |
| | Arginine | 3.1% (3) | 7% (13) | 9.3% (25) | 6.4% |
| Negatively charged | Aspartate | 2% (2) | 5.4% (10) | 3.3% (9) | 7.6% |
| | Glutamate | 5.1% (5) | 4.3% (8) | 3.3% (9) | 7.0% |

Fig. 12

```
AGCAGTGGTATCAACGCAGAGTACGCGGGAGTCCAGGTCCAGCTTCGTCAGGAGTTGGAC   60
ACACAATATACGGTGCTCTTGCTACTTCCACACCTGATGACGACCATAATGTTGGTGATC  120
                                      M   T   T   I   M   L   V   I      8
CTCCTTGTGGGGGCGTGTGTCGCCATACCACCCGGCCGTCCAACAGACAGCATCAGGTTC  180
  L   L   V   G   A   C   V   A   I   P   P   G   R   P   T   D   S   I   R   F    28
GTTCGGCAGACAAAACCTTTACCCCGTCCGCAACACCCACAGATCTCGCCCACACCCCCT  240
  V   R   Q   T   K   P   L   P   R   P   Q   H   P   Q   I   S   P   T   P   P    48
GCTGGCTACCAACCCAAGCCCCAGGTAGATCCAACCCCGCACCCAGGTCATGTCATCCAG  300
  A   G   Y   Q   P   K   P   Q   V   D   P   T   P   H   P   G   H   V   I   Q    68
ACTCTACCAGCACATCCAAGTTCAAAACTGACCAGGCCTGCTCCACGACCCTCGCGACAC  360
  T   L   P   A   H   P   S   S   K   L   T   R   P   A   R   P   S   R   H       88
CAACGCAGCGCAGACGAAGTTCGACAGGGAAGTGTTCCTACCACCGCAATAGGCAAGCCC  420
  Q   R   S   A   D   E   V   R   Q   G   S   V   P   T   T   A   I   G   K   P   108
CAGACTCTGCCTCCCAAGTCCCAACTTACAAAACCAGCTGTACGGCCACAAACTCGTCCA  480
  Q   T   L   P   P   K   S   Q   L   T   K   P   A   V   R   P   Q   T   R   P   128
GCTACTCTTCCTGGGAATCTGGCTAAACCTGCTCAGCGATCCAAGAGTCTTGAAGACAGC  540
  A   T   L   P   G   N   L   A   K   P   A   Q   R   S   K   S   L   E   D   S   148
AGCTTCGCTCCTCTTCCTACTGGGCCCATTGTGGAACCAAGACCTTCCCCAGGAGAGCTG  600
  S   F   A   P   L   P   T   G   P   I   V   E   P   R   P   S   P   G   E   L   168
ACAAAACCAGCTAGTCGCCCCATTGTTGATCCCATACCTCCCGCAGGAGAACTGACAAAA  660
  T   K   P   A   S   R   P   I   V   D   P   I   P   P   A   G   E   L   T   K   188
CCAGCTAGTCGCCCCATTGTTGATCCCATACCTCCCGCAGGAGAACTGACAAAACCAGCT  720
  P   A   S   R   P   I   V   D   P   I   P   P   A   G   E   L   T   K   P   A   208
AGTCGCCCCATTGTTGATCCCATACCTCCCGCAGGAGAACTGACAAAACCAGCTAATCGT  780
  S   R   P   I   V   D   P   I   P   P   A   G   E   L   T   K   P   A   N   R   228
CCCAAGAGTGTGGATAGTGGTTTTGCTCCACTACCTACTGGACCCATTGTAGAACCCAGA  840
  P   K   S   V   D   S   G   F   A   P   L   P   T   G   P   I   V   E   P   R   248
CCACCTCCGGGAGAGCTAACAAAACCAGCTCCTCGTCCTAGGCCTCGTCCAGGGGACTTA  900
  P   P   P   G   E   L   T   K   P   A   P   R   P   R   P   R   P   G   D   L   268
ACAAAACCAGCCACTCGTCCCAGGCCTCGTCCTGCGCGTCCCACACAGGCATAAAGTTTC  960
  T   K   P   A   T   R   P   R   P   R   P   A   R   P   T   Q   A   *           285
GTCTATCCCGACGTCTCATTTGCACCTGATAAGCGATAAAATC                                     1003
```

Fig. 13

```
TACGCGGGGCATTTGGTCTCTGCAGCATCCGTCTTCATCATGAGGGCAGTCGTGTGTGTG    60
                                              M  R  A  V  V  C  V    7
CTTCTCGCTATTTCCGGAATGGCAAGTGCCCAGTCAGCGAGAGGCGAAACGTTTGCGCAT   120
 L  L  A  I  S  G  M  A  S  A  Q  S  A  R  G  E  T  F  A  H     27
GCCAGACCATCTGTCAACAGCTTCCAGGACTCTGCTTCCCTCTCTGCTGATCCTTCTGCT   180
 A  R  P  S  V  N  S  F  Q  D  S  A  S  L  S  A  D  P  S  A     47
GCTGCGGCTCCTCGAGCAGCCCCTGCAGCAGCCCCTGCCGCAGCTCCTGCCGCAGCTCCC   240
 A  A  A  P  R  A  A  P  A  A  A  P  A  A  A  P  A  A  A  P     67
GCACAGCAGAACTATGGGCCAAATTTCTTCGGTCCAGGACTCAACAATCCATTGGCCTTC   300
 A  Q  Q  N  Y  G  P  N  F  F  G  P  G  L  N  N  P  L  A  F     87
CCTCTCAATCCATTGGTAGCACAGCAAGCCCAGAGGATCGCTTCCTTCAACCCCAACCTC   360
 P  L  N  P  L  V  A  Q  Q  A  Q  R  I  A  S  F  N  P  N  L    107
AGAGTGTTCGTTGATATTGACGGCTCAGTTCAGCTCACTGATCAGTTCGGCCGCGAAGTT   420
 R  V  F  V  D  I  D  G  S  V  Q  L  T  D  Q  F  G  R  E  V    127
GATGAGGTCTTGGATGAGTTCGGCCGCGATGTATCTGAACTTCTCGATGTCGAAGAGCAG   480
 D  E  V  L  D  E  F  G  R  D  V  S  E  L  L  D  V  E  E  Q    147
CAAGAGGCACTTCTTCGACGTCGCCAGCAGCAACTTGACCTACAGCTGCTGCAGCAGTTC   540
 Q  E  A  L  L  R  R  R  Q  Q  Q  L  D  L  Q  L  L  Q  Q  F    167
AACAACCCTGCCTTTGGTGGTAGTGTTGGTGGACAAGCTGCTGTTGGCGGACAAACTGGT   600
 N  N  P  A  F  G  G  S  V  G  G  Q  A  A  V  G  G  Q  T  G    187
GTTGGGGGAGGATTCCCACGACAGAGATCCTTCAGAATCGTGGTGTAAGACCGCAATGAT   660
 V  G  G  F  P  R  Q  R  S  F  R  I  V  V  *                   202
ACACCTCTTTCAAAGGTCGTAGCTACCACCTATATCACCTTTCCGTTTTTCCTGTCCCCT   720
TCTAACCTCCCTTGCTGATACTCTGGGTCACCTGACCCTGTCATCTGTTACTTTAGGTCA   780
CCTGGTCTTAATTCTTCTTATTTTCCTTCATCTGATAAGTCTTCCTAATTCTGCAACCTC   840
GTCACCTGTTCTTTATCTCTATCCAGAGTATCCTAGCAGACTATCCCAGTGCTTTATCCTA   900
GCAGTGTCCCCCAACACTATTCCGTTGCTCTATTCTGAACGACCCAATTCGTTTACATAT   960
TAAACACCTGTACACGTCTTTACAATAAATTGTAATACATTATTTGTATAAATTATTTA  1020
ATAAAGCAAGACATAAACACAAAACAAAAACAACAAAAAACAAACAACACAAAACAGTAC  1080
TCTGGCGTTGATACCACTGCTTGGCCCTATAGTGAGTCGTATTAG                1125
```

Fig. 14

ACGCGGACAGGTCAGCTATTAGAGTCGCACCAGCAACATCCTCTCCAGCAACATGAAGA 60
                                                       M  K  I    3

TTTTCATTCTCCTTGTGGTGATTGGTGTGGTGTCAGCCCAGCTTGGTGCTGGCCAGGTGG 120
 F  I  L  L  V  V  I  G  V  V  S  A  Q  L  G  A  G  Q  V  G   23

GAGGTGCTGCTCCAGCMCAGGGTGCTGGAGGTGCTGCTGGTGTTGGTGGTCCWGGGGCAG 180
 G  A  A  P  A  Q  G  A  G  G  A  A  G  V  G  G  P  G  A  A   43

CTCCTGTAAACCCCTACGGACCTAAAGTGTATGGTTCTGGCCTCAACAATCCCTTCGCCT 240
  P  V  N  P  Y  G  P  K  V  Y  G  S  L  N  N  P  F  A  F     63

TCCCTCACAACACGTGGGAAGTGAGTCGTGCTGCGGCGGTGGCAGCTACCAACCCCAACC 300
  P  H  N  T  W  E  V  S  R  A  A  A  V  A  A  T  N  P  N  L  83

TCTATGTGCGCGTGGAGTCTGACGGAGGCTGGGAATTCACCAACCGCTTCGGAGAGAAGG 360
  Y  V  R  V  E  S  D  G  G  W  E  F  T  N  R  F  G  E  K  V 103

TTGATGTGTACAACAGCTTCGGCCAAGAGCTTGACTAGTGCAGTCTTTATCTCCTTCTGT 420
  D  V  Y  N  S  F  G  Q  E  L  *                            113

CATTCACCTCATCTCGCCTCTATGAAGGCTGTCACCTCAATAATTTACCCCTCCCATACA 480
TCTGGATGTAAAAAAAACACAGGTTCTGTTGCTCTACAGCCCTGGCTATACAGCAGGTCT 540
GCTGCTACACAGCCCTGGCTATGCAGCAGGTCTGCTGATACACAGCCCTGGCTATACAGC 600
AGGTCTGCTGCTACACAGCCCTGGCTGTGCAGCAGGTCTGCTGATACACAGCCCTGGCTA 660
TGCAGCAGGTCTGCTGCTACACAGCCCTGGCTATGGAGCAGGTCTGCTGCTACACAGCCC 720
TGGTTATGCAGCAGTTCTGCTGTGCAAATCATTAGATACCAATTGGAGTCAGAATAAGAA 780

Fig. 15A

```
GAP 12    33 YGPKVYGSGLNNPFAFPHNTWEVSRAAAVAATN 65
GAP 21    55 YGPNFFGPGLNNPLAFPLNPLVAQQAQRIASFN 87
             ***:..:*.*****:***  *.   ..:*   :*:  *

GAP 12    66 PNLYVRVESDGGWEFTNRFGEKVD-VYNSFGQEL   98
GAP 21    88 PNLRVFVDIDGSVQLTDQFGREVDEVLDEFGRDV 121
             ***  *  *:  **.  ::*::**.:**  *  :.**:::
```

Fig. 15B

Table 2: Physicochemical properties calculated for the GAP 10 deduced protein.

| Amino acid class | Amino acid | GAP 10 |
|---|---|---|
| Non-polar aliphatic | Gly | 18 |
| | Ala | 15 |
| | Val | 10 |
| | Leu | 4 |
| | Ile | 0 |
| | Met | 0 |
| | Total | 47 (47.5%) |
| Aromatic | Phe | 5 |
| | Tyr | 4 |
| | Trp | 2 |
| | Total | 11 (11.1%) |
| Polar uncharged | Ser | 4 |
| | Pro | 8 |
| | Thr | 3 |
| | Cys | 0 |
| | Asn | 8 |
| | Gln | 4 |
| | Total | 27 (27.2%) |
| Positively charged | Lys | 2 |
| | His | 1 |
| | Arg | 3 |
| | Total | 6 (6%) |
| Negatively charged | Asp | 3 |
| | Glu | 5 |
| | Total | 8 (8.1%) |
| Total amino acids | | 99 |
| | Asx | 11 |
| | Glx | 9 |
| | Total | 20 (20.1%) |

Fig. 38

```
ACGCGGGACAGGTCAGCTATTAGAGTCGCACCAGCAACATCCTCTCCAGCAACATGAAGA    60
                                                   M  K  I     3
TTTTCATTCTCCTTGTGGTGATTGGTGTGGTGTCAGCCCAGCTTGGTGCTGGCCAGGTGG   120
 F  I  L  L  V  V  I  G  V  V  S  A▼Q  L  G  A  G  Q  V  G    23
GAGGTGCTGCTCCAGCMCAGGGTGCTGGAGGTGCTGCTGGTGTTGGTGGTCCWGGGGCAG   180
  G  A  A  P  Q  G  A  G  G  A  A  G  V  G  G  P  G  A  A     43
CTCCTGTAAACCCCTACGGACCTAAAGTGTATGGTTCTGGCCTCAACAATCCCTTCGCCT   240
   P  V  N  P  Y  G  P  K  V  Y  G  [S] G  L  N  N  P  F  A  F   63
TCCCTCACAACACGTGGGAAGTGAGTCGTGCTGCGGCGGTGGCAGCTACCAACCCCAACC   300
   P  H  N  T  W  E  V  S  R  A  A  A  V  A  A  T  N  P  N  L   83
TCTATGTGCGCGTGGAGTCTGACGGAGGCTGGGAATTCACCAACCGCTTCGGAGAGAAGG   360
   Y  V  R  V  E [S] D  G  G  W  E  F  T  N  R  F  G  E  K  V   103
TTGATGTGTACAACAGCTTCGGCCAAGAGCTTGACTAGTGCAGTCTTTATCTCCTTCTGT   420
   D  V  Y  N  S  F  G  Q  E  L  D  *                          114
CATTCACCTCATCTCGCCTCTATGAAGGCTGTCACCTCAATAATTTACCCCTCCCATACA   480
TCTGGATGTAAAAAAAACACAGGTTCTGTTGCTCTACAGCCCTGGCTATACAGCAGGTCT   540
GCTGCTACACAGCCCTGGCTATGCAGCAGGTCTGCTGATACACAGCCCTGGCTATACAGC   600
AGGTCTGCTGCTACACAGCCCTGGCTGTGCAGCAGGTCTGCTGATACACAGCCCTGGCTA   660
TGCAGCAGGTCTGCTGCTACACAGCCCTGGCTATGGAGCAGGTCTGCTGCTACACAGCCC   720
TGGTTATGCAGCAGTTCTGCTGTGCAAATCATTAGATACCAATTGGAGTCAGAATAAGAA   780
CAGTCAATTTTGGCTGTGATAAAAACGATAAAATCTTGAATTTTGTAAGCTTTCATGTAA   840
ATATTTATTTCTACACGTCTCTCTCTCTCTCTCTCTCTCTCTCTCTCTCTCTCTCTCTCT  900
CTCTAAGTCATCTCAAAACACAACCGCTCGACTCTATAGCCCATGAAGGTGTGAGCTTTT   960
CCTTATCCTCCTGTCCTAGGTGTTCACAAGTGCTCAGTAGTGTTCACCAGTGTTCACACG  1020
TGTCCACATGTGCCCACAAGCGTTCACTAGTGTTCAGCAGTGTTCACCAGCATTCAGCAG  1080
TGTTTAGCAGCGTTCAGCAGTGTTCAGCAGCGTTCACCACGGAGGATTCAGAACTATGGC  1140
ACACCTGGCATGGAGTTTTGGCTGCCCTGTGATAACACACACGTCTACTGCTCCCTCTA  1200
TCAGGGGAAATTTTGACTGAAAAACTATAACTTCAGTAATTATAAACATTGATTATATGTA  1260
AATAAACATATAGACAGT                                            1278
```

Fig. 39

SEQUENCE LISTING

<160> NUMBER OF SEQ ID NOS: 32

<210> SEQ ID NO 1
<211> LENGTH: 548
<212> TYPE: PRT
<213> ORGANISM: Cherax quadricarinatus

<400> SEQUENCE: 1

```
Met Ile Arg Arg Val Thr Thr Pro Leu Leu Ala Leu Leu Leu Ala Gly
1               5                   10                  15

Trp Val Val Ala Gln Thr Thr Asp Met Asp Pro Glu Gln Tyr Cys Ala
            20                  25                  30

Arg Arg Asp Asp Glu Tyr Phe Arg Lys Asp Phe Gly Asp Pro Ala Glu
        35                  40                  45

Phe Ala Ser Asp Tyr Arg Ala Asn Cys Gly Val Tyr Tyr Arg Cys Val
50                  55                  60

Pro Ala Pro Ala Gly Lys Arg Ser Ile Ser Ala Ser Gln Cys Gln Ser
65                  70                  75                  80

Glu Leu Phe Phe Asp Val Gln Gln Gln Ile Cys Glu Arg Lys Ser Lys
                85                  90                  95

Val Thr Asn Cys Glu Gln Ile Asp Lys Glu His Pro Pro Gln Pro Phe
            100                 105                 110

Trp Pro Leu Arg Glu Gly Glu Ser Gln Cys Lys Ser Gly Glu Ile
        115                 120                 125

Met Cys Gly Ser Gly Glu Cys Leu Pro Gln His Arg Phe Cys Asp Glu
    130                 135                 140

Asn Ser Asp Cys Ala Asp Gly Ser Asp Glu Asn Ile Cys Thr Pro Asp
145                 150                 155                 160

Lys Asp Pro Asn Arg Ala Asp Val Cys Glu Pro Arg Thr Cys Leu Trp
                165                 170                 175

Ser Gln Gly Cys Phe Cys Ser Val Asp Gly Thr Arg Ile Pro Gly Asp
            180                 185                 190

Leu Thr Val Asp Gln Thr Pro Gln Met Ile Thr Ile Thr Phe Thr Gly
        195                 200                 205

Ala Ile Asn Glu Arg Asn Phe Arg Ile Phe Gln Asp Val Phe Lys Asp
    210                 215                 220

Thr Val Lys His Lys Gly Asn Asp Cys Thr Pro Lys Gly Thr Phe Phe
225                 230                 235                 240

Ile Ser His Gly Phe Ser Asn Tyr Ser Ala Ile Gln Glu Leu Asn Arg
                245                 250                 255

Val Gly His Glu Ile Ala Val Ser Ser Ile Thr Asn Asn Asp Asn Pro
            260                 265                 270

Asp Tyr Trp Ser Lys Leu Ser Ala Leu Asp Tyr Glu Ala Glu Met Asp
        275                 280                 285

Gly Ala Arg Leu Ile Ile Glu Lys Phe Ala Asn Ile Thr Ala Asn Glu
    290                 295                 300

Val Leu Gly Ile Arg Val Pro Lys Gln Arg Val Gly Gly Asn Arg Gln
305                 310                 315                 320

Phe Arg Met Met Val Asp Trp Gly Phe Leu Tyr Asp Ser Ser Ile Ser
                325                 330                 335

Ala Pro Met Gly Arg Leu Pro Leu Trp Pro Tyr Thr Leu Met His Arg
            340                 345                 350

Met Pro His Lys Cys Leu Gly Asn Asp Gln Asn Cys Pro Ser Gln Asn
        355                 360                 365
```

```
Phe Thr Val Trp Glu Met Val Ile Asn Glu Met Asp Arg Arg Asp Asp
    370                 375                 380

Pro Gln Phe Asp Glu Arg Leu Thr Gly Cys His Phe Val Asp Gln Cys
385                 390                 395                 400

Ala Asn Ile Gln Ser Pro Glu Gln Phe Arg Ala Phe Leu Asp Asn Asn
            405                 410                 415

Leu Ala Arg His Tyr Arg Thr Asn Arg Ala Pro Leu Gly Leu His Phe
        420                 425                 430

Thr Ser Gly Tyr Phe Glu Thr Arg Arg Asp Phe Leu Arg Glu Phe Val
            435                 440                 445

Lys Trp Val Arg Glu Thr Ala Leu Ser Gly Asp Tyr Phe Phe Val Thr
450                 455                 460

Met Gln Gln Val Ile Asn Trp Met Glu Ala Pro Thr Glu Leu Thr Ala
465                 470                 475                 480

Ile Asn Asn Phe Gln Glu Trp Lys Gly Lys Cys Glu Val Lys Gly Gln
                485                 490                 495

Pro Tyr Cys Ser Leu Pro Asn Pro Cys Pro Lys Lys Val Pro Arg Ile
            500                 505                 510

Phe Pro Asn Glu Glu Met Phe Leu Tyr Thr Cys Met Glu Cys Pro
            515                 520                 525

Asn Thr Tyr Pro Trp Leu Gly Asp Pro His Gly Asn Gly Phe Leu Asp
530                 535                 540

Ile Pro Asp Phe
545

<210> SEQ ID NO 2
<211> LENGTH: 11
<212> TYPE: PRT
<213> ORGANISM: Cherax quadricarinatus

<400> SEQUENCE: 2

Leu Phe Gln Asp Val Phe Lys Asp Ala Glu Lys
1               5                   10

<210> SEQ ID NO 3
<211> LENGTH: 13
<212> TYPE: PRT
<213> ORGANISM: Cherax quadricarinatus

<400> SEQUENCE: 3

Leu Ser Ala Leu Asp Tyr Glu Ala Glu Met Asp Gln Arg
1               5                   10

<210> SEQ ID NO 4
<211> LENGTH: 15
<212> TYPE: PRT
<213> ORGANISM: Cherax quadricarinatus

<400> SEQUENCE: 4

Ala Pro Leu Gly Leu His Phe Thr Ser Gly Tyr Phe Glu Thr Arg
1               5                   10                  15

<210> SEQ ID NO 5
<211> LENGTH: 19
<212> TYPE: PRT
<213> ORGANISM: Cherax quadricarinatus

<400> SEQUENCE: 5

Met Met Val Asp Trp Gly Phe Leu Tyr Asp Ser Ser Leu Ser Ala Pro
1               5                   10                  15
```

Met Gly Arg

<210> SEQ ID NO 6
<211> LENGTH: 11
<212> TYPE: PRT
<213> ORGANISM: Cherax quadricarinatus

<400> SEQUENCE: 6

```
His Gly Val Glu Leu Ala Val Ser Ser Leu Thr
1               5                   10
```

<210> SEQ ID NO 7
<211> LENGTH: 16
<212> TYPE: PRT
<213> ORGANISM: Cherax quadricarinatus

<400> SEQUENCE: 7

```
His Met Val Asp Gln Cys Ala Asn Leu Lys Ser Pro Glu Lys Phe Arg
1               5                   10                  15
```

<210> SEQ ID NO 8
<211> LENGTH: 13
<212> TYPE: PRT
<213> ORGANISM: Cherax quadricarinatus

<400> SEQUENCE: 8

```
Glu Leu Phe Phe Asp Val Gln Gln Gln Leu Cys Glu Arg
1               5                   10
```

<210> SEQ ID NO 9
<211> LENGTH: 285
<212> TYPE: PRT
<213> ORGANISM: Cherax quadricarinatus

<400> SEQUENCE: 9

```
Met Thr Thr Ile Met Leu Val Ile Leu Val Gly Ala Cys Val Ala
1               5                   10                  15

Ile Pro Pro Gly Arg Pro Thr Asp Ser Ile Arg Phe Val Arg Gln Thr
                20                  25                  30

Lys Pro Leu Pro Arg Pro Gln His Pro Gln Ile Ser Pro Thr Pro Pro
            35                  40                  45

Ala Gly Tyr Gln Pro Lys Pro Gln Val Asp Pro Thr Pro His Pro Gly
        50                  55                  60

His Val Ile Gln Thr Leu Pro Ala His Pro Ser Ser Lys Leu Thr Arg
65                  70                  75                  80

Pro Ala Pro Arg Pro Ser Arg His Gln Arg Ser Ala Asp Glu Val Arg
                85                  90                  95

Gln Gly Ser Val Pro Thr Thr Ala Ile Gly Lys Pro Gln Thr Leu Pro
            100                 105                 110

Pro Lys Ser Gln Leu Thr Lys Pro Ala Val Arg Pro Gln Thr Arg Pro
        115                 120                 125

Ala Thr Leu Pro Gly Asn Leu Ala Lys Pro Ala Gln Arg Ser Lys Ser
    130                 135                 140

Leu Glu Asp Ser Ser Phe Ala Pro Leu Pro Thr Gly Pro Ile Val Glu
145                 150                 155                 160

Pro Arg Pro Ser Pro Gly Glu Leu Thr Lys Pro Ala Ser Arg Pro Ile
                165                 170                 175

Val Asp Pro Ile Pro Pro Ala Gly Glu Leu Thr Lys Pro Ala Ser Arg
            180                 185                 190
```

```
Pro Ile Val Asp Pro Ile Pro Pro Ala Gly Glu Leu Thr Lys Pro Ala
        195                 200                 205

Ser Arg Pro Ile Val Asp Pro Ile Pro Pro Ala Gly Glu Leu Thr Lys
    210                 215                 220

Pro Ala Asn Arg Pro Lys Ser Val Asp Ser Gly Phe Ala Pro Leu Pro
225                 230                 235                 240

Thr Gly Pro Ile Val Glu Pro Arg Pro Pro Gly Glu Leu Thr Lys
            245                 250                 255

Pro Ala Pro Arg Pro Arg Pro Arg Gly Asp Leu Thr Lys Pro Ala
            260                 265                 270

Thr Arg Pro Arg Pro Arg Pro Ala Arg Pro Thr Gln Ala
        275                 280                 285

<210> SEQ ID NO 10
<211> LENGTH: 9
<212> TYPE: PRT
<213> ORGANISM: Cherax quadricarinatus

<400> SEQUENCE: 10

Pro Ala Thr Leu Pro Phe His Ala Lys
1               5

<210> SEQ ID NO 11
<211> LENGTH: 6
<212> TYPE: PRT
<213> ORGANISM: Cherax quadricarinatus

<400> SEQUENCE: 11

Ser Gln Leu Thr Lys Pro
1               5

<210> SEQ ID NO 12
<211> LENGTH: 5
<212> TYPE: PRT
<213> ORGANISM: Cherax quadricarinatus

<400> SEQUENCE: 12

Glu Leu Pro Pro Lys
1               5

<210> SEQ ID NO 13
<211> LENGTH: 16
<212> TYPE: PRT
<213> ORGANISM: Cherax quadricarinatus

<400> SEQUENCE: 13

Gln Gly Ser Val Pro Thr Thr Gln Leu Gln Val Lys Pro Asp Pro Pro
1               5                   10                  15

<210> SEQ ID NO 14
<211> LENGTH: 16
<212> TYPE: PRT
<213> ORGANISM: Cherax quadricarinatus

<400> SEQUENCE: 14

Pro Leu Val Asp Pro Leu His Gly Asn Cys Pro Cys Cys Asn Tyr Arg
1               5                   10                  15

<210> SEQ ID NO 15
<211> LENGTH: 19
<212> TYPE: PRT
<213> ORGANISM: Cherax quadricarinatus
```

-continued

<400> SEQUENCE: 15

Trp Asp Ser Gly Phe Ala Pro Leu Pro Thr Gly Pro Leu Val Glu Arg
1               5                   10                  15

Pro Arg Val

<210> SEQ ID NO 16
<211> LENGTH: 15
<212> TYPE: PRT
<213> ORGANISM: Cherax quadricarinatus

<400> SEQUENCE: 16

Glu Asp Ser Ser Phe Ala Gln Leu Trp Phe Thr Val Glu Pro Arg
1               5                   10                  15

<210> SEQ ID NO 17
<211> LENGTH: 202
<212> TYPE: PRT
<213> ORGANISM: Cherax quadricarinatus

<400> SEQUENCE: 17

Met Arg Ala Val Val Cys Val Leu Leu Ala Ile Ser Gly Met Ala Ser
1               5                   10                  15

Ala Gln Ser Ala Arg Gly Glu Thr Phe Ala His Ala Arg Pro Ser Val
                20                  25                  30

Asn Ser Phe Gln Asp Ser Ala Ser Leu Ser Ala Asp Pro Ser Ala Ala
            35                  40                  45

Ala Ala Pro Arg Ala Ala Pro Ala Ala Ala Pro Ala Ala Ala Pro Ala
        50                  55                  60

Ala Ala Pro Ala Gln Gln Asn Tyr Gly Pro Asn Phe Phe Gly Pro Gly
65                  70                  75                  80

Leu Asn Asn Pro Leu Ala Phe Pro Leu Asn Pro Leu Val Ala Gln Gln
                85                  90                  95

Ala Gln Arg Ile Ala Ser Phe Asn Pro Asn Leu Arg Val Phe Val Asp
            100                 105                 110

Ile Asp Gly Ser Val Gln Leu Thr Asp Gln Phe Gly Arg Glu Val Asp
        115                 120                 125

Glu Val Leu Asp Glu Phe Gly Arg Asp Val Ser Glu Leu Leu Asp Val
130                 135                 140

Glu Glu Gln Gln Glu Ala Leu Leu Arg Arg Arg Gln Gln Gln Leu Asp
145                 150                 155                 160

Leu Gln Leu Leu Gln Gln Phe Asn Asn Pro Ala Phe Gly Gly Ser Val
                165                 170                 175

Gly Gly Gln Ala Ala Val Gly Gly Gln Thr Gly Val Gly Gly Gly Phe
            180                 185                 190

Pro Arg Gln Arg Ser Phe Arg Ile Val Val
        195                 200

<210> SEQ ID NO 18
<211> LENGTH: 11
<212> TYPE: PRT
<213> ORGANISM: Cherax quadricarinatus

<400> SEQUENCE: 18

Glu Val Glu Glu Leu Leu Asp Glu Phe Gly Arg
1               5                   10

<210> SEQ ID NO 19

-continued

<210> SEQ ID NO 19
<211> LENGTH: 12
<212> TYPE: PRT
<213> ORGANISM: Cherax quadricarinatus

<400> SEQUENCE: 19

Ser Thr Ala Ala Ala Pro Ala Ala Ala Ala Ala Arg
1               5                   10

<210> SEQ ID NO 20
<211> LENGTH: 12
<212> TYPE: PRT
<213> ORGANISM: Cherax quadricarinatus

<400> SEQUENCE: 20

Pro Leu Asn Pro Leu Val Ala Gln Gln Ala Gln Arg
1               5                   10

<210> SEQ ID NO 21
<211> LENGTH: 17
<212> TYPE: PRT
<213> ORGANISM: Cherax quadricarinatus

<400> SEQUENCE: 21

Val Phe Val Asp Val Asp Gly Ser Ala His Phe Thr Asp Gln Phe Gly
1               5                   10                  15

Arg

<210> SEQ ID NO 22
<211> LENGTH: 17
<212> TYPE: PRT
<213> ORGANISM: Cherax quadricarinatus

<400> SEQUENCE: 22

Asp Val Ser Glu Leu Leu Asp Val Gln Glu Gln Glu Gln Leu Ala
1               5                   10                  15

Arg

<210> SEQ ID NO 23
<211> LENGTH: 10
<212> TYPE: PRT
<213> ORGANISM: Cherax quadricarinatus

<400> SEQUENCE: 23

Cys Asn Leu Asn Asn Pro Leu Ala Leu Val
1               5                   10

<210> SEQ ID NO 24
<211> LENGTH: 114
<212> TYPE: PRT
<213> ORGANISM: Cherax quadricarinatus

<400> SEQUENCE: 24

Met Lys Ile Phe Ile Leu Leu Val Val Ile Gly Val Val Ser Ala Gln
1               5                   10                  15

Leu Gly Ala Gly Gln Val Gly Gly Ala Ala Pro Ala Gln Gly Ala Gly
                20                  25                  30

Gly Ala Ala Gly Val Gly Gly Pro Gly Ala Ala Pro Val Asn Pro Tyr
            35                  40                  45

Gly Pro Lys Val Tyr Gly Ser Gly Leu Asn Asn Pro Phe Ala Phe Pro
        50                  55                  60

His Asn Thr Trp Glu Val Ser Arg Ala Ala Ala Val Ala Ala Thr Asn
65                  70                  75                  80

```
Pro Asn Leu Tyr Val Arg Val Glu Ser Asp Gly Gly Trp Glu Phe Thr
            85                  90                  95

Asn Arg Phe Gly Glu Lys Val Asp Val Tyr Asn Ser Phe Gly Gln Glu
            100                 105                 110

Leu Asp

<210> SEQ ID NO 25
<211> LENGTH: 113
<212> TYPE: PRT
<213> ORGANISM: Cherax quadricarinatus

<400> SEQUENCE: 25

Met Lys Ile Phe Ile Leu Leu Val Val Ile Gly Val Ser Ala Gln
1               5                   10                  15

Leu Gly Ala Gly Gln Val Gly Gly Ala Ala Pro Ala Gln Gly Ala Gly
            20                  25                  30

Gly Ala Ala Gly Val Gly Gly Pro Gly Ala Ala Pro Val Asn Pro Tyr
            35                  40                  45

Gly Pro Lys Val Tyr Gly Ser Gly Leu Asn Asn Pro Phe Ala Phe Pro
            50                  55                  60

His Asn Thr Trp Glu Val Ser Arg Ala Ala Ala Val Ala Ala Thr Asn
65                  70                  75                  80

Pro Asn Leu Tyr Val Arg Val Glu Ser Asp Gly Gly Trp Glu Phe Thr
            85                  90                  95

Asn Arg Phe Gly Glu Lys Val Asp Val Tyr Asn Ser Phe Gly Gln Glu
            100                 105                 110

Leu

<210> SEQ ID NO 26
<211> LENGTH: 12
<212> TYPE: PRT
<213> ORGANISM: Cherax quadricarinatus

<400> SEQUENCE: 26

Val Glu Ser Asp Gly Gly Trp Glu Phe Thr Asn Arg
1               5                   10

<210> SEQ ID NO 27
<211> LENGTH: 14
<212> TYPE: PRT
<213> ORGANISM: Cherax quadricarinatus

<400> SEQUENCE: 27

Ala Ala Ala Val Ala Ala Thr Asn Pro Leu Asn Tyr Val Arg
1               5                   10

<210> SEQ ID NO 28
<211> LENGTH: 21
<212> TYPE: PRT
<213> ORGANISM: Cherax quadricarinatus

<400> SEQUENCE: 28

Val Tyr Gly Ser Gly Leu Asn Asn Pro Phe Ala Phe Pro His Ser Gln
1               5                   10                  15

Trp Glu Val Ser Arg
            20

<210> SEQ ID NO 29
<211> LENGTH: 12
```

<212> TYPE: PRT
<213> ORGANISM: Cherax quadricarinatus

<400> SEQUENCE: 29

Ala Gly Val Gly Gly Lys Pro Ala His Pro Val Lys
1               5                   10

<210> SEQ ID NO 30
<211> LENGTH: 74
<212> TYPE: PRT
<213> ORGANISM: Cherax quadricarinatus

<400> SEQUENCE: 30

Gln Tyr Cys Ala Arg Arg Asp Asp Glu Tyr Phe Arg Lys Asp Phe Gly
1               5                   10                  15

Asp Pro Ala Glu Phe Ala Ser Asp Tyr Arg Ala Asn Cys Gly Val Tyr
                20                  25                  30

Tyr Arg Cys Val Pro Ala Pro Ala Gly Lys Arg Ser Ile Ser Ala Ser
            35                  40                  45

Gln Cys Gln Ser Glu Leu Phe Phe Asp Val Gln Gln Gln Ile Cys Glu
        50                  55                  60

Arg Lys Ser Lys Val Thr Asn Cys Glu Gln
65                  70

<210> SEQ ID NO 31
<211> LENGTH: 38
<212> TYPE: PRT
<213> ORGANISM: Cherax quadricarinatus

<400> SEQUENCE: 31

Gln Cys Lys Ser Gly Glu Ile Met Cys Gly Ser Gly Glu Cys Leu Pro
1               5                   10                  15

Gln His Arg Phe Cys Asp Glu Asn Ser Asp Cys Ala Asp Gly Ser Asp
                20                  25                  30

Glu Asn Ile Cys Thr Pro
            35

<210> SEQ ID NO 32
<211> LENGTH: 138
<212> TYPE: PRT
<213> ORGANISM: Cherax quadricarinatus

<400> SEQUENCE: 32

Val Asp Gln Thr Pro Gln Met Ile Thr Ile Thr Phe Thr Gly Ala Ile
1               5                   10                  15

Asn Glu Arg Asn Phe Arg Ile Phe Gln Asp Val Phe Lys Asp Thr Val
                20                  25                  30

Lys His Lys Gly Asn Asp Cys Thr Pro Lys Gly Thr Phe Phe Ile Ser
            35                  40                  45

His Gly Phe Ser Asn Tyr Ser Ala Ile Gln Glu Leu Asn Arg Val Gly
        50                  55                  60

His Glu Ile Ala Val Ser Ser Ile Thr Asn Asn Asp Asn Pro Asp Tyr
65                  70                  75                  80

Trp Ser Lys Leu Ser Ala Leu Asp Tyr Glu Ala Glu Met Asp Gly Ala
                85                  90                  95

Arg Leu Ile Ile Glu Lys Phe Ala Asn Ile Thr Ala Asn Glu Val Leu
                100                 105                 110

Gly Ile Arg Val Pro Lys Gln Arg Val Gly Gly Asn Arg Gln Phe Arg
            115                 120                 125

```
                      -continued

Met Met Val Asp Trp Gly Phe Leu Tyr Asp
    130                 135
```

STABLE AMORPHOUS CALCIUM CARBONATE COMPRISING SYNTHETIC PHOSPHORYLATED PEPTIDES

CROSS REFERENCE TO RELATED APPLICATIONS

The present application is a divisional of U.S. patent application Ser. No. 12/765,009, filed on Apr. 22, 2010, which is a continuation-in-part of International Application No. PCT/IL2008/001362 filed on Oct. 22, 2008, which claims priority under 35 U.S.C. § 119 to Israeli Patent Application No. 186850 filed on Oct. 22, 2007 and to Israeli Patent Application No. 193461 filed on Aug. 14, 2008, which are incorporated herein by reference in their entireties.

FIELD OF THE INVENTION

The present invention relates to compositions comprising amorphous calcium carbonate, and to methods of preparing same, and further to compositions comprising phosphorylated amino acids or peptides. Particularly, said peptides are selected from crustacean proteins, including GAP65, GAP22, GAP21, and GAP12 (also referred to herein interchangeably as "GAP10"). Pharmaceutical and nutraceutical compositions comprising amorphous calcium carbonate and phosphorylated amino acids or peptides are provided.

BACKGROUND OF THE INVENTION

Calcium plays one of the central roles in the signal transduction, and further it is an important structural element in biological systems. From protozoa to vertebrata, deposited calcium salts helps to keep rigid bodily shapes of animals, calcium phosphate being the main component of endoskeletons in the vertebrates and calcium carbonate of exoskeletons in the invertebrates. Calcified exoskeletons with calcium carbonate minerals as the main constituents are widespread among echinoderms, mollusks, and arthropods, providing protection and serving as calcium storage. Some crustaceans store calcium carbonate temporarily, in an amorphous state, which makes it better available, particularly for quick mobilization during the mineralization of their new exoskeleton structures after molting. In freshwater crayfish, the calcium carbonate deposits comprise a pair of disc-like structures, known as gastroliths, that are located on each side of the stomach wall. Gastrolith formation takes place in the gastrolith pouch, a cavity formed between the columnar epithelium of the gastrolith disc and the cardiac stomach wall. The main functions of the gastrolith disc epithelium are the transport of hemolymph calcium to the gastrolith and the synthesis of the gastrolith organic matrix. The formation of amorphous calcium carbonate in the living bodies of, for example, crayfish is rather intriguing, since amorphous minerals are usually thermodynamically unstable. Amorphous calcium carbonate (ACC) tends to transform to its crystalline polymorphs, mainly calcite and aragonite, WO 2005/11541.4 employs crustacean organs for providing compositions with stable ACC which is readily available for human consumption. In view of the general metabolic and biomechanical importance of calcium, and since ACC is a potentially more soluble and absorbable form of calcium carbonate as a dietary supplements, it is an object of the invention to provide new methods for preparing amorphous calcium carbonate.

It is another object of this invention to provide pharmaceutical and nutraceutical compositions comprising stable ACC.

Other objects and advantages of present invention will appear as description proceeds.

SUMMARY OF THE INVENTION

The present invention relates to a composition comprising amorphous calcium carbonate (ACC) and at least one component selected from phosphorylated amino acids and phosphorylated peptides. Said phosphorylated amino acids and phosphorylated peptides may comprise phospho-serine or phospho-threonine or both. Said phosphorylated amino acids and phosphorylated peptides stabilize the amorphous form of said calcium carbonate in the composition of the invention. In one aspect of the invention, said phosphorylated peptide originates from crustacean gastrolith. In one embodiment, the composition of the invention comprises ACC, at least one phosphorylated amino acid or peptide, and optionally at least one additional component such as chitin or chitosan.

According to another specific embodiment, the composition of the invention comprises ACC, at least one phosphorylated peptide selected from GAP65, GAP22, GAP21, and GAP12 (also indicated herein as GAP10) and optionally, an additional component.

In another aspect, the present invention relates to a peptide comprising an amino acid sequence selected from the group consisting of SEQ ID NO:1, SEQ ID NO:9, SEQ ID NO:17, SEQ ID NO:24, SEQ ID NO:25 or any homologues, variants, derivatives or fragments thereof. In another aspect, the present invention relates to new crustacean peptides and their use in affecting the crystalline state of calcium carbonate and in the preparation of formulations. The invention also relates to functional fragments of said peptides. Non limiting examples of such functional fragments are the GAP10 (also indicated as GAP12) fragment as denoted by SEQ ID NO. 25 and the GAP65 fragments as denoted by SEQ ID NO. 30, 31 and 32. The isolated proteins related to below include GAP65, GAP22, GAP21, and GAP12 (also indicated herein as GAP10) (were GAP stands for gastrolith protein); deduced amino acid sequences of said new proteins are provided herein, and they are denoted as SEQ. ID. NOS: 1, 9, 17, 24 and 25. The invention provides an isolated and purified crustacean peptide comprising essentially a sequence selected from the group consisting of SEQ ID NO:1, SEQ ID NO:9, SEQ ID NO:17, SEQ ID NO:24, SEQ ID NO:25 and homologues thereof. A sequence homolog according to the invention is a peptide with any insertions, deletions, and substitutions, as far as at least 90% of the sequence is preserved. More specifically, at least about 80% to 100% homology. The invention further includes an isolated and purified peptide comprising in its sequence a subsequence, said subsequence being a fragment of the above said crustacean GAP peptides, preferably a subsequence at least ten amino acid long. Said subsequence may have a sequence selected from, for example, SEQ ID NOS: 2 to 8, SEQ ID NOS: 10 to 16, and SEQ ID NOS: 18 to 23, or other fragments of sequences SEQ ID NO:1, SEQ ID NO:9, SEQ ID NO:17 or SEQ ID NO:24. Examples for such fragments may be SEQ ID NO:25 that is a fragment of GAP10 (also indicated as GAP12) as denoted by SEQ ID NO. 24, and the three domains of GAP65 as denoted by SEQ ID NO. 30, 31 and 32.

The invention provides a composition comprising one or more peptides as defined above, or their derivatives or variants or functional fragments or mixtures thereof together with amorphous calcium carbonate (ACC). Said peptide stabilizes the amorphous form of said calcium carbonate in said composition. The term "functionally equivalent fragment, derivative, or variant" as used herein includes peptides with modifications that do not interfere with their ability to inhibit calcium carbonate crystallization thereby stabilizing the amorphous form of calcium carbonate. More specifically, the terms "homologues" and "derivatives" as used herein mean peptides or polypeptides, containing any insertions, deletions, substitutions and modifications that do not interfere with their function. A derivative should maintain a minimal homology to the amino acid sequence comprised within said molecules, e.g. between at least 80% to 100%, specifically, between at least 82% to 98%, more specifically, between at least 84% to 96%, more specifically, between at least 86% to 94%, more specifically, between at least 88% to 92%, most specifically, at least 90%. In specific embodiments, derivatives of the invention maintain a minimal homology to the amino acid sequence comprised within said molecules, of between at least 94%, at least 95%, at least 96%, at least 97%, at least 98%, at least 99% or at least 99.5%. It should be appreciated that by the term "insertions" as used heroin is meant any addition of amino acid residues to the protein molecules of the invention or any fragments thereof, between 1 to 10 amino acid residues, particularly any one of 1, 2, 3, 4, 5, 6, 7, 8, 9 and 10 amino acid residues. Similarly, the term "deletion" is meant any removal of amino acid residues to the protein molecules of the invention or any fragments thereof, between 1 to 10 amino acid residues, particularly any one of 1, 2, 3, 4, 5, 6, 7, 8, 9 and 10 amino acid residues.

The term "derivative" is used to define amino acid sequence variants, and covalent modifications of a polypeptide or peptide made use of in the present invention. e.g. of a specified sequence. The functional derivatives of a polypeptide or peptide utilized according to the present invention, e.g. of a specified sequence, preferably have at least about 80%, more preferably at least about 82%, even more preferably at least about 84%, even more preferably at least about 86%, even more preferably at least about 86%, even more preferably at least about 88%, most preferably at least about 90% overall sequence homology with the amino acid sequence of a peptide or polypeptide as structurally defined above, e.g. of a specified sequence. The functional derivatives of a polypeptide or peptide utilized according to the present invention, e.g. of a specified sequence, may also have at least about 92%, at least 94%, at least 96% and even at least 98% overall sequence homology with the amino acid sequence of a peptide or polypeptide as structurally defined above.

"Homology" with respect to a native peptide or polypeptide and its functional derivative is defined herein as the percentage of amino acid residues in the candidate sequence that are identical with the residues of a corresponding native peptide or polypeptide, respectively, after aligning the sequences and introducing gaps, if necessary, to achieve the maximum percent homology, and not considering any conservative substitutions as part of the sequence identity. Neither N- nor C-terminal extensions nor insertions shall be construed as reducing identity or homology. Methods and computer programs for the alignment are well known.

The term "amino acid sequence variant" or "variant" refers to molecules with some differences in their amino acid sequences as compared to a peptide or polypeptide as defined herein, e.g. of a specified sequence. Substitutional variants are those that have at least one amino acid residue removed and a different amino acid inserted in its place at the same position in a polypeptide as defined herein, e.g. of a specified sequence. These substitutions may be single, where only one amino acid in the molecule has been substituted, or they may be multiple, where two or more amino acids have been substituted in the same molecule. Insertional variants are those with one or more amino acids inserted immediately adjacent to an amino acid at a particular position in a polypeptide as defined herein, e.g. of a specified sequence. Immediately adjacent to an amino acid means connected to either the □-carboxy or □-amino functional group of the amino acid. Deletional variants are those with one or more amino acids in a polypeptide according to the present invention, e.g. of a specified sequence, removed. Ordinarily, deletional variants will have one or two amino acids deleted in a particular region of the molecule.

Variants of the peptides and polypeptides of the invention may have at least 80% sequence similarity, often at least 82% sequence similarity, 84% sequence similarity, 86% sequence similarity, 88% sequence similarity, or at least 90%, 92%, 94%, 96%, or 98% sequence similarity at the amino acid level, with the protein or peptide of interest.

The terms "fragments" and "functional fragments" used herein mean the polypeptides and peptides of the invention or any fragments thereof, with any insertions, deletions, substitutions and modifications, that maintain biological function, such that they inhibit the crystallization of calcium carbonate. Non-limiting examples of such fragments are provided in SEQ ID NO:25, a fragment of GAP10, and in SEQ ID NO:30-32, fragments of GAP65.

The term "peptide" is used herein to denote a peptide, polypeptide or protein. The peptide may be obtained synthetically, through genetic engineering methods, expression in a host cell, or through any other suitable means. Unless indicated otherwise, a peptide is generally composed of naturally-occurring L-amino acids.

The invention is directed to a peptide having amino acid sequence selected from SEQ ID NO:1, SEQ ID NO:9, SEQ ID NO:17, SEQ ID NO:24, and SEQ ID NO:25, and to peptides being their sequence homologous having, preferably, at least 90% to 99.9% homology. It should be further appreciated that any nucleic acid sequence, specifically a DNA or cDNA sequence encoding a peptide according to the invention is a part of the invention as well. Specific examples for such nucleic acid sequences are disclosed by FIGS. 1, 13, 14, 15 and 39. Provided in the invention is a calcium carbonate preparation containing a peptide as defined above or its derivative.

In a preferred embodiment of the invention, a calcium carbonate preparation comprising ACC is provided, said preparation being stable at least for about one month to about one year. A method of preparing stable amorphous calcium carbonate is disclosed, which comprises mixing in aqueous phase in any order a soluble salt comprising calcium, a carbonate source, and a phosphorylated amino acid or phosphorylated peptide. Said source may, for example, comprise a carbonate salt dissolved in the liquid phase, or said source may comprise gaseous carbon dioxide.

The term "stable" as used herein means not taking part readily in chemical change. Specifically, the polypeptides and peptides of the invention, such as GAP65, GAP22, GAP21, GAP12 (also indicated as GAP10) and any functional peptides, derivatives, homologues and variants thereof, interact with calcium carbonate to inhibit its crystallization, and thus, said mixture is deemed stable as long as said inhibition persists and calcium carbonate crystallization is prevented or reduced. The stabilizing effect of said polypeptides and peptides is illustrated in Example 6 and FIGS. 7, 8 and 9.

In some embodiments, the amorphous calcium carbonate preparation (ACC) of the invention is stable for at least about one week to about two weeks, two weeks to about three weeks, three weeks to about one month, one month to about a month and a half, a month and a half to about two months, two months to about two months and a half, two months and a half to about three months, three months and a half to about four months, four months to about four months and a half, four months and a half to about five months, five months to about five months and a half, five months and a half to about six months, six months to about six months and a half, six months and a half to about seven months, seven months to about seven months and a half, seven months and a half to about eight months, eight months to about eight months and a half, eight months and a half to about nine months, nine months to about nine months and a half, nine months and a half to about ten months, ten months to about ten months and a half, ten months and a half to about eleven months, or eleven months and a half to about a year.

In specific embodiments, the ACC preparation is stable in room temperature, said temperature ranging from about 10° C. to about 45° C., more specifically, 12° C. to about 30° C., more specifically, 14° C. to about 28° C., more specifically, 16° C. to about 27° C., more specifically, 18° C. to about 26° C., more specifically, 19° C., 20° C., 21° C., 22° C., 23° C., 24° C., or, most specifically, 25° C.

The invention provides a pharmaceutical formulation comprising the above said composition, containing one or more phosphorylated amino acids, or phosphorylated peptides as defined herein or their derivatives or variants or functional fragments or mixtures thereof, together with ACC. The above said composition is, in other aspect of the invention, advantageously used as a nutraceutical formulation, for example as a food additive. Said pharmaceutical formulation is preferably orally administered and may comprise fillers or solvents or additives. Thus, according to another aspect, the invention provides a dietary supplement comprising the above said composition, and further optionally other components selected from the group consisting of chitin, chitosan, and fillers. Said pharmaceutical formulation is preferably used in treating, preventing or ameliorating conditions such as bone metabolism disorders, pain, proliferative diseases, neurological disorders, immunologic disorders, cardiovascular diseases, pulmonary diseases, nutritional disorders, reproductive disorders, musculoskeletal disorders, and dental problems. Said treating may lead to disappearance of causative factors or to mitigating the symptoms. Said proliferative disease may be, for example, breast carcinoma or bronchogenic carcinoma. Said treating may comprise slowing down or inhibiting the cell proliferation in a tumor. As for said pain, it may be postoperative pain, pain after injury, pain associated with cancer, and neuropathic pain. The mentioned neurological disorder is, for example, selected from demyelinating diseases, dementias, and movement disorders. Said condition may be a degenerative disease selected from multiple sclerosis, Alzheimer's disease, and Parkinson's disease. Said condition may comprise a bone or bone marrow disorder, which may be, for example fracture or osteoporosis. According to another embodiment, the condition treated by the composition of the invention may be a neurodegenerative disorder.

Said new peptides GAP65, GAP22, GAP21, and GAP12 (OR GAP10) or their derivatives are used, in one aspect of the invention, in the manufacture of medicaments. Also provided is a method of treating a bone disorder or injury, and a method of managing pain, comprising orally administering a formulation comprising calcium carbonate and one or more of said new peptides or their derivatives. The term "derivatives" as used herein includes also peptide products obtained by alkylation, esterification, neutralization, cyclization, or oligomerization.

The invention provides a method of inhibiting the crystallization of calcium carbonate in a mixture comprising a carbonate and a calcium salt, comprising admixing into said mixture an amount of a phosphorylated amino acid or a phosphorylated peptide. Said phosphorylated amino acid or a phosphorylated peptide preferably comprises phosphoserine or phospho-threonine.

The term crystallization as used herein refers to the natural or artificial process of formation of solid crystals precipitating from a solution, melt or more rarely deposited directly from a gas. The crystallization process consists of two major events, nucleation and crystal growth. Nucleation is the step where the solute molecules dispersed in the solvent start to gather into clusters, on the nanometer scale (elevating solute concentration in a small region), that becomes stable under the current operating conditions. These stable clusters constitute the nuclei. However when the clusters are not stable, they redissolve. Therefore, the clusters need to reach a critical size in order to become stable nuclei. Such critical size is dictated by the operating conditions (temperature and supersaturation, for example). It is at the stage of nucleation that the atoms arrange in a defined and periodic manner that defines the crystal structure.

Thus, the term "inhibition of crystallization" as used herein refers to any action that interferes with the processes of crystallization as described, i.e. nucleation and crystal growth. Such interference may be, as a non limiting example, the disruption of electrostatic forces between molecules comprising the forming crystal, or prevention of a localized elevated concentration of the crystallizing molecule.

The term "inhibition" as referred to herein, relates to the retardation, retraining or reduction of a process by any one of about 1% to 5%, about 5% to 10%, about 10% to 15%, about 15% to 20%, about 20% to 25%, about 25% to 30%, about 30% to 35%, about 35% to 40%, about 40% to 45%, about 45% 20 to 50%, about 50% to 55%, about 55% to 60%, about 60% to 65%, about 65% to 70%, about 75% to 80%, about 80% to 85% about 85% to 90%, about 90% to 95%, about 95% to 99%, or about 99% to 99.9%.

The invention provides, in one embodiment, a method of inhibiting the crystallization of calcium carbonate, comprising admixing into the crystallization or precipitation mixture an inhibitory effective amount of at least one peptide comprising an amino acid sequence selected from SEQ ID NO:1, SEQ ID NO:9, SEQ ID NO:17, SEQ ID NO:24 and SEQ ID NO:25, or any homolog or functional fragment or derivative or variant, or of a mixture or combination thereof. A method of inhibiting the crystallization of calcium carbonate according to the invention is provided, comprising providing a calcium salt soluble in water, and contacting said salt with at least one peptide selected from GAP65, GAP22, GAP21, and GAP12 (also indicated herein as GAP10), or with any functionally equivalent fragment, derivative, or variant thereof, or with any mixture or combination thereof.

In one aspect of the invention, food additives or functional foods are provided, comprising a mixture of calcium carbonate and at least one phosphorylated amino acid or peptide; said at least one peptide, in one embodiment, having a sequence selected from the group consisting of SEQ ID NO:1, SEQ ID NO:9, SEQ ID NO:17, SEQ ID NO:24, SEQ ID NO:25 and any homologues, variants, derivatives or fragments thereof.

BRIEF DESCRIPTION OF THE DRAWINGS

The above and other characteristics and advantages of the invention will be more readily apparent through the following examples, and with reference to the appended drawings, wherein:

FIG. 1A—SDS-PAGE Coomassie staining of the soluble proteins profile of the gastrolith, compared to molecular weight reference proteins (left), SDS-PAGE of fraction 17 containing GAP65 purified by DEAE column chromatography stained with Coomassie, "stains all", and "pas" (right); FIG. 1B—chromatogram of GAP65 obtained by nanospray Qtof2 following tryspin digestion, sequences of the peptides (as denoted by SEQ ID NO. 2 to 8) from significant peaks were obtained through MSIMS analysis;

FIGS. 2A-C. comprises the complete deduced amino acid sequence of GAP65 and it bioinformatic analysis; FIG. 2A—deduced amino acid sequence of the open reading frame of GAP65 (also denoted by SEQ ID NO. 1), in bold is predicted signal sequence, grey boxes are possible phosphorylation sites, dark boxes at amino acids no. 72 and 173 are predicted O-glycosylation sites, light boxes are predicted N-glycosylation sites; FIG. 2B—a scheme of the GAP65 sequence showing the predicted domains: ChtBD2 is chitin binding domain 2, LDLa is low-density lipoprotein receptor domain class A, and the last one is polysaccharide deacetylase domain; FIG. 2C-3D structure of the LDLa domain based on homology to lipoprotein receptor, on the left is the NMR structure of complement-like repeat CR3 from the low density lipoprotein receptor-related protein, on the right is the predicted structure of the LDLa domain of GAP65;

FIG. 3A—detection of GAP65 expression during premolt using RT-PCR, RNA was sampled from gastrolith epithelial disc, hepatopancreas, sub-epidermal tissue, sperm duct, and stomach wall, elongation factor 2 (Eft2) was used to reassure RNA extraction, control for genomic contamination was used; FIG. 3B—localization of GAP65 expression by in situ hybridization in induced premolt and intact intermoit males, left panel represents the hematoxylin and eosin staining (H&E), middle panel represents the negative control sense—GAP65 probe, the two right panels represent the CAP65 anti-sense probe with the last being an enlargement of a specific area, the bar represents 200 am except for induced premolt sense probe where the bar represents 100 um;

FIGS. 5A-C. are photos showing morphological deformities of the gastroliths following GAP65 silencing, representative gastroliths are dissected from crayfish injected with either of ecdysone and dsRNA of GAP65 (left), ecdysone and dsRNA carrier (middle), ecdysone carrier and dsRNA carrier (right); FIG. 5A—lateral view of whole gastroliths dissected from the crayfish; FIGS. 5B and 5C—X-ray imaging of the above gastrolith prior to dissection (dorsal view);

FIGS. 6A and 6B—cross sections of the central part of the gastrolith demonstrating the mineral and matrix arrangement (X 50, X 200, respectively); FIG. 6C—mineral arrangement comprising nano-spherules (X 15000); the ecdysone without GAP shows normal gastrolith appearance, while the ecdysone+GAP65 dsRNA treated gastrolith appears deformed;

FIGS. 7A-B. show SEM images of in vitro precipitated calcium carbonate in the presence/absence of the gastrolith purified protein; FIG. 7A—calcium carbonate precipitate with GAP65 enriched fraction (left), calcium carbonate precipitated with equivalent amount of trypsin as a control (right); FIG. 7B—a SEM image of ACC 40 days after the precipitation, demonstrating typical amorphous structures with nanospheres of 50-500 nm;

FIG. 8A—Raman spectra of calcium carbonate obtained by precipitation with GAP65 enriched fraction; FIG. 8B—27 days after the precipitation; FIG. 8C—6.5 month after the precipitation;

FIG. 10A shows GAP22 and trypsin digestion peptides thereof, denoted as SEQ ID NOs 10 to 16; FIG. 10B shows GAP21 and trypsin digestion peptides thereof, denoted as SEQ ID NOs 18-23; FIG. 10C shows GAP12 (as also indicated herein as GAPE) and trypsin digestion peptides thereof, denoted as SEQ ID NOs 25-28;

FIG. 11. shows Raman spectra of the calcium carbonate precipitated from the solution of calcium chloride and sodium carbonate in the presence of gastrolith extract;

FIG. 12, is Table 1, showing amino acid compositions of GAP proteins;

FIG. 13. shows nucleotide sequence of GAP22 cDNA and the corresponding deduced amino acid sequence in open reading frame (also denoted by SEQ ID NO. 9); the asterisks indicate stop codons and the gray highlighted sequences are the untranslated regions; the putative signal peptides in the N-terminus are underlined;

FIG. 14. shows nucleotide sequence of GAP21 cDNA and the corresponding deduced amino acid sequence in open reading frame (also denoted by SEQ ID NO. 17); the symbols have the same meaning as in FIG. 13;

FIGS. 15A-B. relate to the GAP sequences; FIG. 15A shows a partial nucleotide sequence of GAP12 (also indicated herein as GAP10) cDNA and the corresponding deduced amino acid sequence in open reading frame (also denoted by SEQ ID NO. 25); the symbols have the same meaning as in FIG. 13; FIG. 15B is sequence alignment of GAP12 (OR GAP10) and GAP21, amino acid positions of the two proteins are shown on the right and left, sequence identities are indicated by "*" conserved substitutions are indicated by ":", and semi-conserved substitutions are indicated by ".";

FIG. 16. to FIG. 27 show Raman Spectra described in detail in Examples 9 to 20;

FIG. 33A, left: SDS-PAGE stained with Coomassie blue; middle: Staining of the same gel for phosphoproteins; right: transfer of the same fraction to a nitrocellulose membrane and incubation with $^{46Ca+2}$. Spots identified as GAP10 by LC-MS are circled. Abbreviations: PC (positive control). FIG. 33B: shows the identification of GAP10 peptides by LC-MS; the identified peptides are underlined on the GAP10 sequence, and the related peaks are indicated on the spectrum;

FIG. 36A: total RNA was extracted from the gastrolith disc, hypodermis, hepatopancreas, muscle, and sperm-duct; ribosomrnal 18S unit was used to confirm RNA extraction; genomic control with gastrolith disc RNA was used; FIG. 36B H&E staining; 1: tissue probed with the negative control sense, GAP10 probe; 2: tissue probed with the GAP10 antisense probe; 3: with the far right image corresponding to an enlargement of a specific area. Abbreviations: Ga (gastrolith disc), Mac (muscle tissue). (Scale bar: 200 pm, except for in the enlarged box, where it represents 20 pm);

FIG. 37A: top view of representative gastroliths, dissected from crayfish injected with ecdysone (left) or ecdysone and GAP10 dsRNA (right). FIG. 37B: Topographic images of representative surface samples from each group. FIG. 37C: real-time RT.PCR relative quantification of GAP10 transcript levels in the gastrolith disc as calculated for each experimental group injected with ecdysone (n=5; empty bars) or ecdysone and GAP10 dsRNA (n=6; black bars) and mean Swedish height (SH) as calculated for the two groups (n=3 and n=4 respectively). *—represents statistically significant difference of P<0.01. **—represents statistically significant difference of P<0.001.

FIG. 38. is Table 2, showing physicochemical properties calculated for the GAP 10 deduced protein; amino acid composition is categorized according to side chain properties; percentage of amino acids corresponding to the total of each category is indicated in brackets; and FIG. 39. shows nucleotide sequence of GAP 10 cDNA and deduced amino acids of its open reading frame (also denoted by SEQ ID NO.24); the 5' and 3' UTRs are highlighted in gray; the putative signal peptide in the N.terminus is underlined; arrowhead indicates signal peptide cleavage site; predicted phosphorylation sites are boxed; italic letters indicate AAP[AIVI, GGX and An consensus sequences; the asterisk indicates a stop codon.

DETAILED DESCRIPTION OF THE INVENTION

It has now been found that some phosphorylated amino acids or peptides affect the precipitation of calcium carbonate in vitro, leading to the formation of amorphous form of calcium carbonate. Particularly, the effects have been observed when said peptides comprise several proteins present in the late premolt gastrolith of *Cherax quadricarinatus*. Peptides having apparent molecular weights of approximately 65 kDa, 22 kDa, 21 kDa, and 12 kDa induce precipitation of nanospheres of amorphous calcium carbonate material; in comparison, an inert protein provides $CaCO_3$ crystals. The nanoparticles show a Raman shift typical for amorphous $CaCO_3$.

Figure 11:
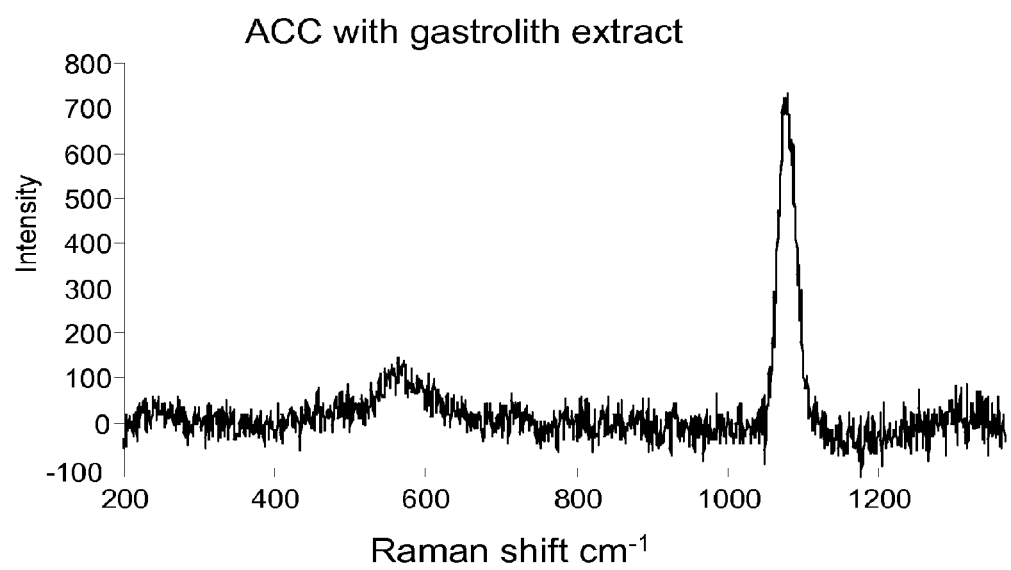

The above proteins, denoted as GAP65, GAP22, GAP21, GAP12 (also indicated as GAP10), respectively, according to their apparent molecular weights estimated by SDS-PAGE, are involved in the precipitation and stabilization of ACC. The gastrolith extract which contains said four proteins inhibits calcium carbonate crystallization and stabilizes the amorphous form of calcium carbonate (ACC). ACC was detected by Raman spectrometry in a precipitate of $CaCO_3$ prepared from a solution containing $CaCl_2$, $Na_2CO_3$ and the gastrolith extract (FIG. 11). The presence of ACC is validated by the presence of a predominant peak at about 1080 $cm^{-1}$. Expressions of the GAP genes were found to be specific to the gastrolith epithelial disc and sub-epidermal tissue, both are cuticle related tissues. Specific expressions of the GAP peptides in several target tissues by means of RT-PCR was also studied. For example, the expression of GAP65 was found in more cuticle related tissues, whereas the expression of GAP22 was found rather in the gastrolith epithelial disc.

The cDNA sequences of the corresponding genes were obtained and their deduced proteins were found (FIGS. 2, 13-15 and 39). All four proteins were found to contain signal peptides at their N-terminus (underlined amino acids in FIGS. 13-15 and 39, bold in FIG. 2). Similarity search against databases of conserved domains revealed that GAP65 contains three conserved domains: Chitin-binding domain 2, Low density lipoprotein receptor domain class A, and Polysaccharide deacetylase domain. GAP 12, GAP 21 and GAP 22, on the other hand, show no significant similarity to any known domain. Blast alignment of GAP 12 and GAP 21 revealed a 46.3% identity in the deduced amino acid sequences of these proteins (FIG. 15). Physico-chemical analysis of the deduced proteins revealed, that the calculated molecular weights of GAPs 12, 21 and 65 are smaller than expected, 9.9, 19.5 and 60.8 kDa respectively, while that of GAP 22 is higher than expected, 28.6 kDa (Table 1). GAP 12, GAP 21 and GAP 65 have an acidic pI, therefore they are negatively charged at the physiological pH of the gastrolith (near pH 8.7). GAP 12 and GAP 21 have a high percentage of non-polar, aliphatic amino acids (glycine, alanine and valine) and a high percentage of the polar but uncharged amino acid proline (highlighted in gray in Table 1). GAP65 has a high content of acidic amino acids. GAP22 has a basic pI, therefore it is positively charged at the physiological pH of the gastrolith. Its main characteristics are a high percentage of the polar but uncharged amino acid proline and of the positively charged arginine.

Due to special features of the new proteins, provided in this invention is also a method of inhibiting the crystallization of calcium carbonate, comprising admixing into the crystallization or precipitation mixture an amount of GAP65 or a functional fragment thereof, or a derivative, or a variant thereof. In other aspect of the invention, a method is provided of inhibiting the crystallization of calcium carbonate, comprising contacting a calcium salt soluble in water with GAP65 or a functional fragment, derivative, or variant thereof.

Figure 1A:
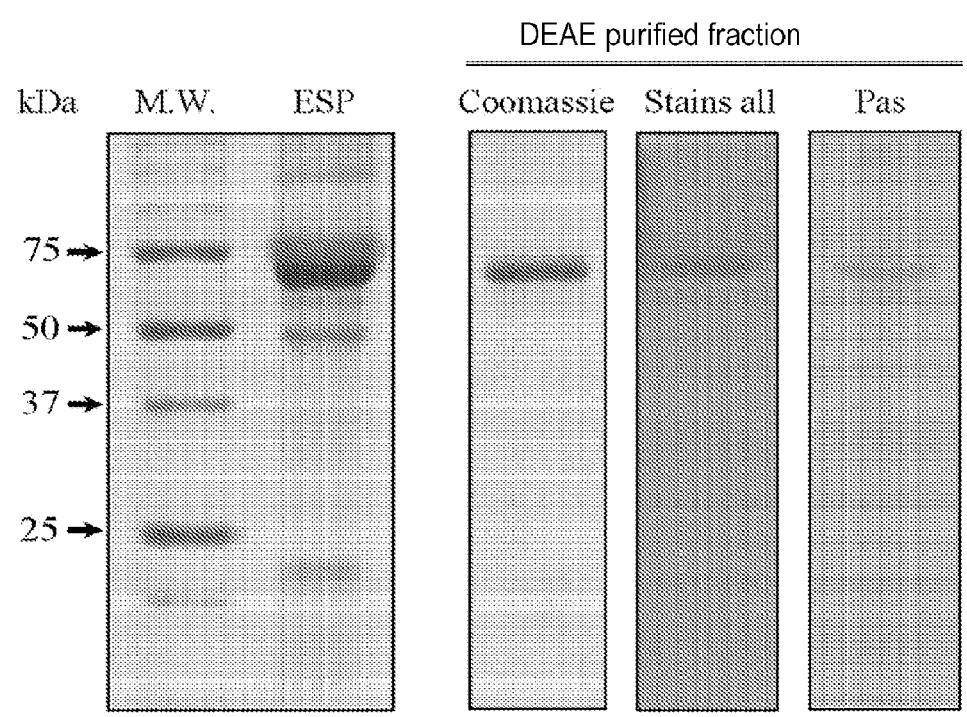
FIGS. 1A-B. show the isolation of gastrolith soluble proteins, purification and partial sequencing of GAP65.
Figure 1B:
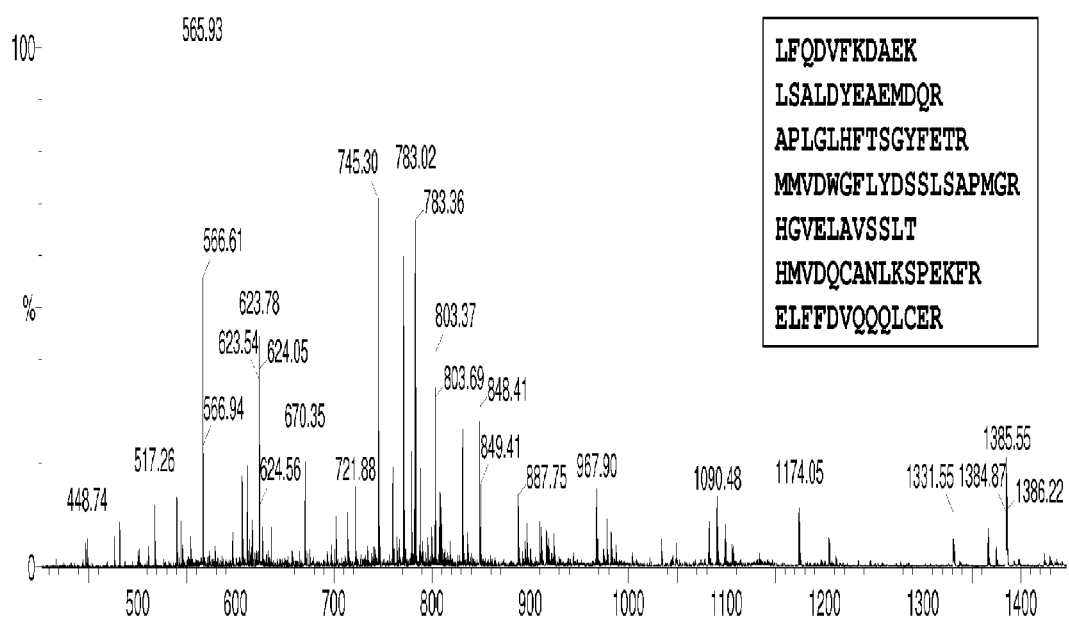
Figure 2A:
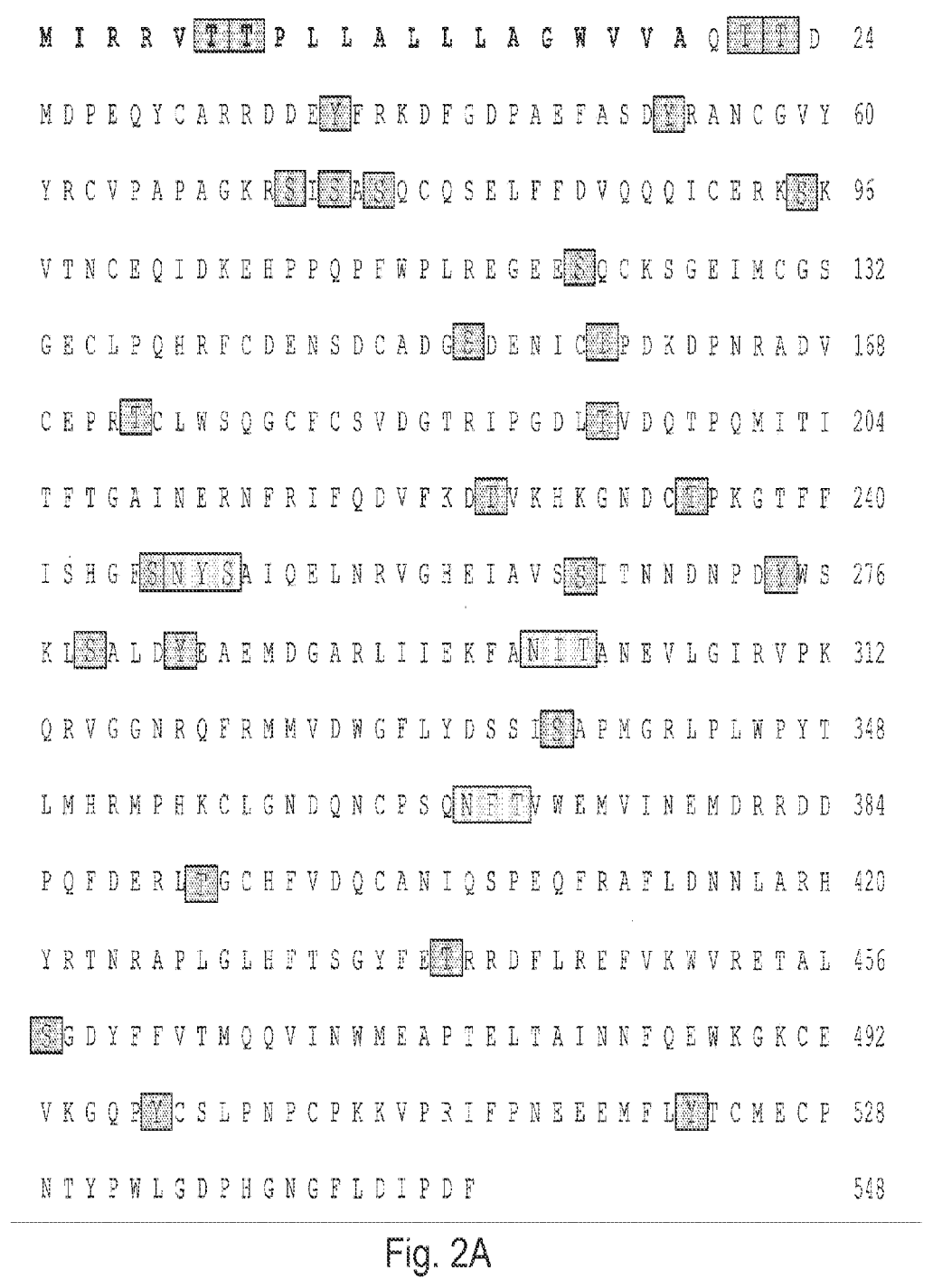
Figure 2B:
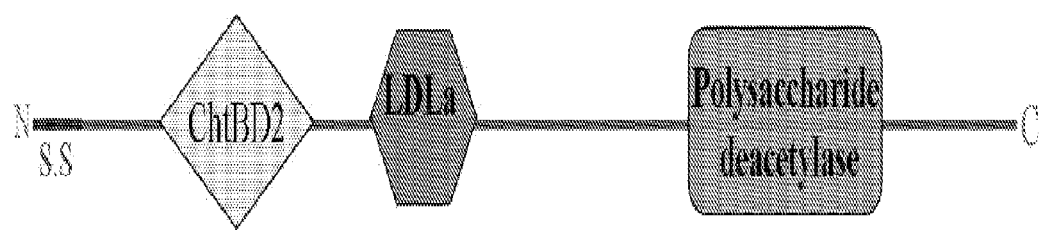
Figure 3A:
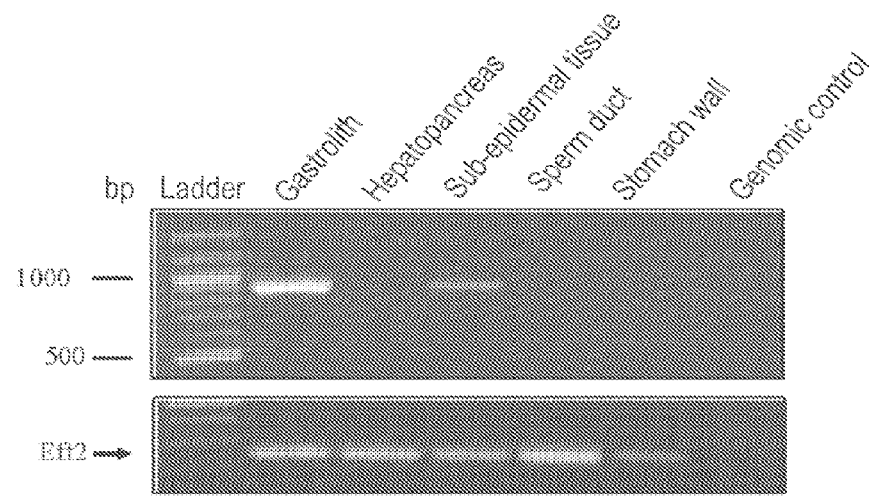
FIGS. 3A-B. show specific expression of GAP65 and its localization in the columnar epithelium of tho gastrolith during induced premolt.
Figure 4:
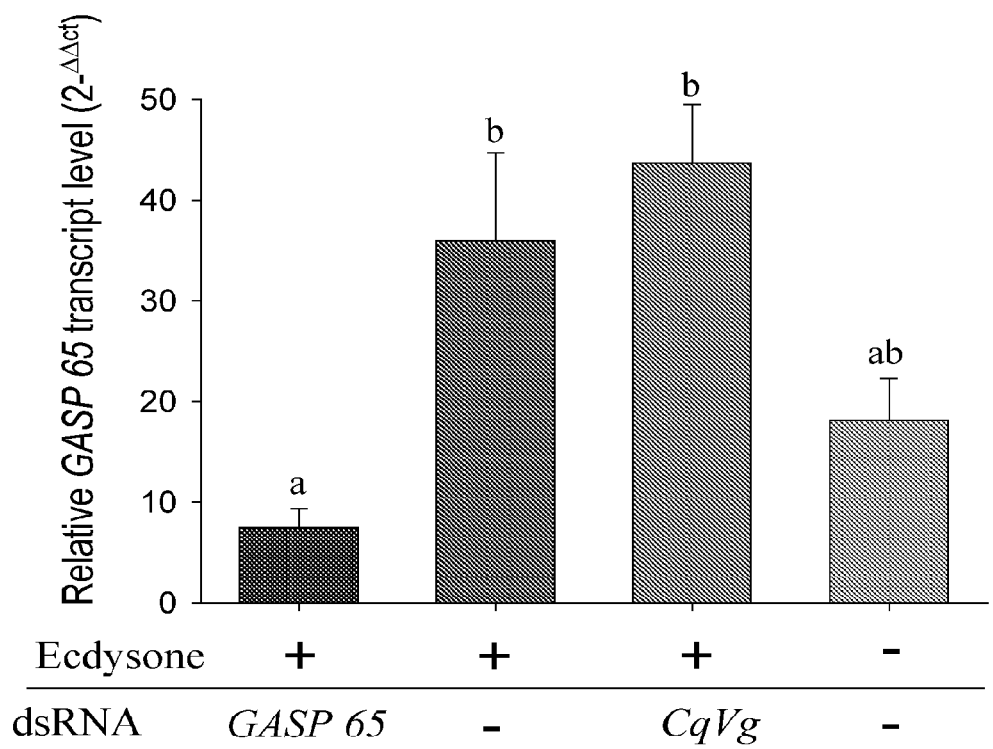
FIG. 4. shows relative transcript level of GAP65 (denoted GASP 65) in the gastrolith disc following GAP65 silencing, relative quantitation of GAP65 transcript level using real-time RT-PCR in the gastrolith disc of crayfish injected with (left to right): ecdysone and dsRNA of GAP65, ecdysone and dsRNA carrier, ecdysone and dsRNA of *C quadricarinatus* vitellogenin (CqVg), ecdysone carrier and dsRNA carrier, and the letters represent statistical significance.

GAP65 was purified from gastrolith soluble protein extract by ion exchange chromatography, and was identified as a negatively charged glycopeptide, containing about 12 mol % Asp+Glu, based on SEQ. ID. NO. 1. Sequencing of the peptides by MS-MS provided seven oligopeptide subsequences (SEQ. ID. NO. 2-8; FIG. 1B) which were used for the construction of degenerative primers for the acquisition of a complete GAP65 encoded gene sequence based on gastrolith epithelial disc mRNA. The total deduced amino acid sequence revealed a 548 amino acids long peptide (SEQ. ID. NO. 1; FIG. 2A). Bioinformatic analysis of GAP65 sequence suggested the presence of three known domains (FIG. 2B): chitin binding domain 2 (ChtBD2) from amino acids 29-102 (also denoted by SEQ ID NO. 30), low-density lipoprotein receptor domain class A (LDLa), from amino acids 122-159 (also denoted by SEQ ID NO. 31), and polysaccharide deacetylase domain from amino acids 195-332 (also denoted by SEQ ID NO. 32). The LDLa domain has a predicted calcium binding property. Expression of GAP65 was tested in premolt crayfish in several target tissues by means of RT-PCR, and was detected in the gastrolith epithelial disc and in the sub-epidermal tissue, both are cuticle related tissues (FIG. 3A). In situ hybridization visualized the localization of the GAP65 expression in the gastrolith disc of induced premolt and intact intermolt crayfish (FIG. 5B). Relative GAP65 transcript levels in the gastrolith epithelial disc following silencing using GAP65 dsRNA were measured using realtime RT-PCR (FIG. 4). The role of GAP65 in gastrolith formation was tested by an RNAi technique using in vivo injections of GAP65 dsRNA to intermolt crayfish (FIG. 5). The initiation of gastrolith formation was achieved by injection of ecdysone. Morphological deformities of the gastrolith can be observed in crayfish injected with both GAP65 dsRNA and ecdysone (FIG. 5A shows dissected gastrolith, FIGS. 5B and 5C are X-ray views).

It was found that GAP65 essentially affects the micro structure of the crayfish gastrolith. Scanning electron microscope (SEM) micrographs of gastroliths dissected from crayfish injected either with GAP65 dsRNA together with ecdysone or only with ecdysone revealed severe structural abnormalities caused by the absence of GAP65 (FIG. 6). The packaging of the ACC in spherules, and the spherules size, is important for the dense packaging of the gastrolith; the absence of GAP65 led to larger spherules and less condensed structure when compared to the normal gastrolith.

In order to elucidate the role of GAP65 in the biomineralization process, an in vitro calcium carbonate precipitation was performed to test the stabilization of ACC. Electron microscope images of the precipitates distinctly indicated different polymorph composition of calcium carbonate for the precipitation in the presence/absence of GAP65-enriched fractions (FIG. 7). The precipitation of calcium carbonate in the absence of GAP, namely in the presence of an inert protein, resulted in rapid crystallization providing crystals of calcite and/or vaterite as large as 10 μm. On the other hand, the precipitation of calcium carbonate in the presence of GAP65 resulted in amorphous $CaCO_3$ observed as a thin layer consisting of 40-60 nm spherules. The amorphous nature of the calcium carbonate in said spherules was corroborated by Raman spectra, which showed the distinct ACC peak at 1070 $cm^{-1}$, and further by employing powder x-ray diffraction (XRD), which indicated the absence of diffracting peaks from crystalline materials. The presence of GAP65 in the ACC spherules formed by the in vitro precipitation was confirmed by purification of the protein from the spherules and its identification by SDS-PAGE.

$CaCO_3$ deposits obtained by precipitation in the presence of GAP65 were initially characterized by polarized microscope, identifying calcite, vaterite, and ACC. The observations were confirmed by Raman spectroscopy and powder XRD. The ACC constituted about at least 50% of the total $CaCO_3$. The ACC remained stable under room condition for at least 1 months.

Figure 34A:
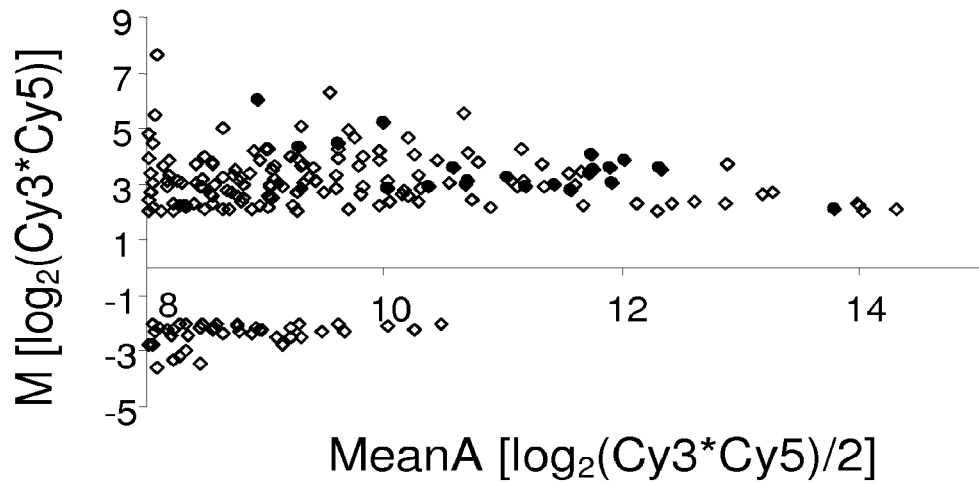
FIG. 34s A-B. shows multigenic expression pattern of gastrolith disc (FIG. 34A) and hypodermis (FIG. 34B) in premolt vs. intermolt crayfish; expression scatter plots of all the ESTs identified as being differentially expressed between the treatment and the control; M, log 2-fold change of normalized emission intensity between the treatment and the control filtered by I M I>2; mean A, $log_2$ of average signal intensity filtered by mean A>9; Cy3 (premolt) and Cy5 (intermolt.control) are normalized microarray signals; empty diamond shapes represent all differentially expressed ESTs; Full circles represent GAP10 ESTs.

GAP10 (also indicated as GAP12) was identified from the extracellular gastrolith matrix. Similarly to GAP65, GAP10 has an acidic pI. The deduced protein sequence (FIG. 39) contains a predicted signal peptide, in accordance with the proteins identification in the extracellular gastrolith matrix. Unlike GAP65, the premolt transcript expression of GAP10 is specific to the gastrolith disc, as shown by RT-PCR and by in situ localization (FIGS. 35A and 35B). Moreover, microarray hybridizations revealed that the transcript of GAP10 is notably highly up-regulated in the gastrolith disc during premolt, while being significantly down-regulated in the hypodermis (FIG. 34), emphasizing the involvement of GAP10 in the construction process of the gastrolith matrix. During premolt, the hypodermis absorbs calcium from the cuticle, while the gastrolith disc deposits that same calcium into the gastrolith. The expression of GAP10 in the hypodermis of intermolt animals, as demonstrated by the microarray results, points to the role of the protein during this particular molt stage.

As mentioned above, GAP10 was not found to have significant similarity to any known proteins in the GenBank database. However, GAP10 does contain several known consensus sequences previously identified in arthropod extracellular structural proteins, including the AAP[A/V] repeat and glycine-rich regions.

Amino acid composition analysis of GAP 10 revealed abundant non-polar, aliphatic amino acids; Gly, Ala and Val, and also polar but uncharged amino acids; Asn and Pro (Table 2, FIG. 38).

The deduced protein sequence of GAP10 does not have predicted chitin-binding domains, neither of the ChtBD2 nor of the R&R type. GAP10 was found to have calcium-binding ability and to be phosphorylated, with two predicted phosphorylation sites at Ser residues.

Figure 37A:
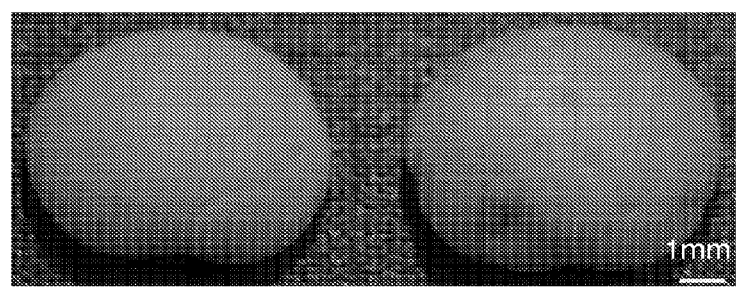
FIGS. 37A-C. relate to the visualization and OPIM measurement of gastrolith surface irregularities and relative transcript levels of GAP10 in the gastrolith disc following GAP10 silencing.
Figure 37B:
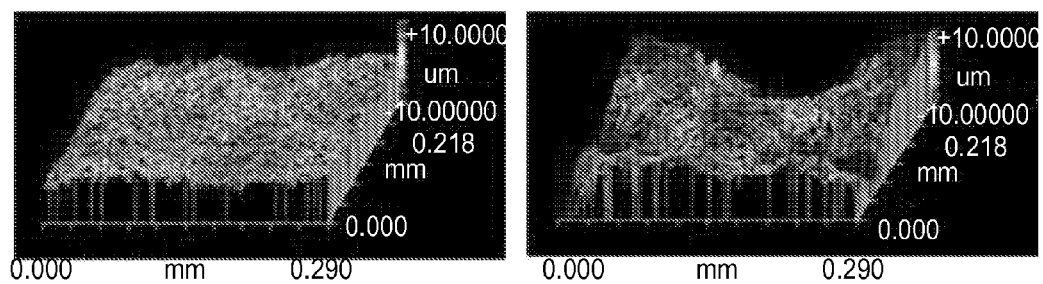

The in vivo silencing of GAP10 was followed by a considerable delay in premolt duration and the development of gastroliths with significant surface irregularities (FIGS. 35, 37A and 37B).

Figure 36:
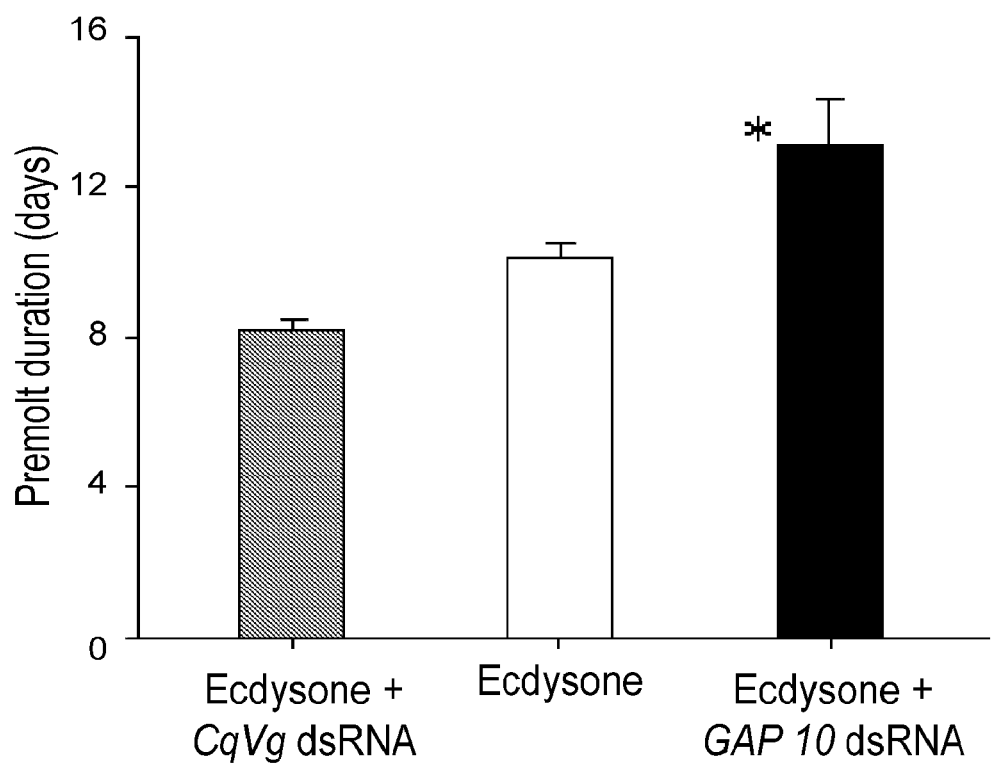
FIG. 36. relates to the prolongation of premolt following GAP10 silencing; Mean premolt duration (the number of days until experiment termination) as calculated for each experimental group injected with ecdysone (n=8; empty bars) or ecdysone and GAP10 dsRNA (n=10; black bars) or ecdysone and CqVg dsRNA (n=6; gray bars); *—represents statistically significant difference of P<0.05.

Administration of ecdysone is known to induce molt in *C. quadricarinatus*. The typical induced premolt duration is 10-14 days until ecdysis, and the peak observed molt mineralization index (MMI) is 0.125-0.145, which is reached 1-2 days before the molt event. In this case, the injections were terminated at MMI=0.1 so as to prevent molting, and premolt duration was calculated up to that point. As shown in FIG. 36, injections of ecdysone together with GAP 10 dsRNA to intermolt animals resulted in an increase in premolt duration, from an a average of 10.1 days in the ecdysone-injected control group to 13.1 days in the group receiving ecdysone and GAP 10 dsRNA. Therefore, the ~10-day mean premolt duration of the ecdysone-induced, non-silenced animals was within the expected range, while the ~13-day mean premolt duration of the silenced animals implies a significant delay.

In summary, GAP10 plays a crucial role in gastrolith formation, since depletion of the protein secreted into the matrix, following transcript silencing, significantly prolonged premolt and was manifested in irregularities appearing exclusively on the surface of the gastroliths, representing the most recently deposited layers. GAP10 is involved in the formation of the chitin-protein-mineral complex of the gastrolith, especially with regards to the deposition of calcium carbonate.

The invention, thus, provides new proteins associated with calcium metabolism in crayfish, which affect the crystalline state of calcium carbonate. Provided is a method of inhibiting the crystallization of calcium carbonate, comprising admixing into the crystallization or precipitation mixture an amount of GAP proteins or functionally equivalent fragments thereof, or derivatives, or variants thereof. The invention relates to a method of preparing ACC by admixing said new protein into a precipitation mixture, namely into a mixture in which the precipitation of $CaCO_3$ occurs, and in which precipitation of crystalline material would occur without said protein. A nonlimiting example of such mixture includes an aqueous solution of calcium chloride comprising GAP65 or GAP10 into which a sodium carbonate solution is added. Of course the order of mixing the components may change, as well as the types of the ions sources. The concentration of GAP65 or GAP10 in the mixture may be, for example, about from 0.05 to 5 wt % based on the weight of $CaCO_3$. The concentration of GAP65 or GAP10 in the precipitation mixture may be, for example, about from 1 to 100 µg/ml.

The instant invention provides a composition containing ACC and a phosphorylated amino acid or peptide, for example a GAP protein. In an important aspect of the invention, a formulation is provided for treating disorders associated with calcium metabolism or signaling, comprising ACC and a stabilizing amount of phosphorylated amino acid or peptide, for example a GAP protein or its derivatives. The formulation is preferably used for oral administration. The formulation of the invention is used as a therapeutic means, or as a therapeutic supplement, or as a nutritional supplement or as a dietary supplement.

In a preferred embodiment of the invention, ACC prepared according to the invention is comprised in a formulation for treating conditions associated with calcium metabolism or calcium signaling. Said conditions may be selected from the group consisting of bone metabolism disorders, pain, proliferative diseases, neurological disorders, immunologic disorders, cardiovascular diseases, pulmonary diseases, nutritional disorders, reproductive disorders, musculoskeletal disorders, and dental problems. Said treating may comprise mitigating the symptoms of the diseases. Said proliferative disease may be selected from sarcomas, carcinomas, lymphomas and melanomas. Said carcinoma is, for example, breast carcinoma or bronchogenic carcinoma. Said treating may lead to shrinking tumors, stopping their growth, or slowing down or inhibiting the cell proliferation in the tumors. Said pain may be selected from postoperative pain, pain after injury, pain associated with cancer, and neuropathic pain. Said neurological disorder may be selected from demyelinating diseases, dementias, and movement disorders; said disorders being, for example, multiple sclerosis, Alzheimer's disease, Parkinson's disease, or other degenerative disease. Said condition to be treated may comprise a bone or bone marrow disorder, such as fracture or osteoporosis. In a preferred embodiment, a composition of the invention is used for treating a neurodegenerative disorder.

The invention relates to a composition of matter comprising ACC and a stabilizing amount of a phosphorylated amino acid (PAA) or a phosphorylated peptide (PP), for example a composition comprising one or more PAA, or one or more PP such as GAP peptides or their functional fragments, derivatives, or variants. The invention also relates to ACC stabilized with PAA, or PP such as GAPs, for use as a medicament or in the manufacture of a medicament, or for use as a food additive.

The process for the preparation of ACC may comprise the steps:
i) Forming an aqueous solution with calcium ions (with $CaCl_2$ solution).
ii) Addition of soluble or insoluble "additives" (phosphoamino acids, chitosan, chitin, synthetic peptides, phosphorylated peptides/proteins or fragments thereof, etc.).
iii) Addition of carbonate ions (with $Na_2CO_3$ solution or another carbonate source, like for example $CO_2$, or $(NH_4)_2CO_3$).
iv) Agitation.
v) Precipitation of $CaCO_3$ slurry (by centrifugation, filtration etc.).
vi) Slurry dehydration (by lyophilizer, air flow, spray drying etc.).

Analysis of the product may comprise testing the resultant $CaCO_3$ by various methods (as XRD, electron diffraction, SEM) to verify its amorphous nature. Raman spectroscopy (RS) was found to be the most efficient and reliable method to characterize ACC. The Raman shifts characteristics of the mineral reported here are the carbonate peak at 1080 $cm^{-1}$ whose broad shape is indicative of ACC and proportional to its content. The phosphate peak at 950 $cm^{-1}$, is proportional to the phosphate content in the sample. Yet, the ratio between 1080 to 950 $cm^{-1}$ is proportional, but not directly indicative of the $CO_3^{2-}/P_4^{3-}$ ratio.

Calcium and carbonate ions, in the solutions from which calcium carbonate was precipitated, was usually in the range of from about 10 mM to about 500 mM. The molar ratio of phosphorylated amino acid (PAA) to calcium was usually in the range of 0.01-0.5. A higher concentration of PAA inhibited the spontaneous precipitation. The chitosan, when present, was in the range of 0.03-0.3 wt %.

Peptides which were extracted from demineralized *Cherax* gastroliths by different proteolytic enzymes (trypsin, papain, and *Streptomyces* protease) induced the formation of ACC. It is suggested that phosphoamino acids and phosphopeptides can induce ACC formation and can stabilize it. It is possible that the intact proteins have additional functions. The Raman spectra and EDS analysis show a significant amount of calcium phosphate similar to the ACC induced by total insoluble matrix (ISM), suggesting that the phosphate in the ISM is associated to the proteins.

The precipitated calcium carbonate was checked over long periods for the amorphous/crystalline state. It was found that the samples of ACC obtained by methods of the invention were stable at room temperature for more than seven months, keeping their amorphous state.

EXAMPLES

Example 1

Figure 2C:
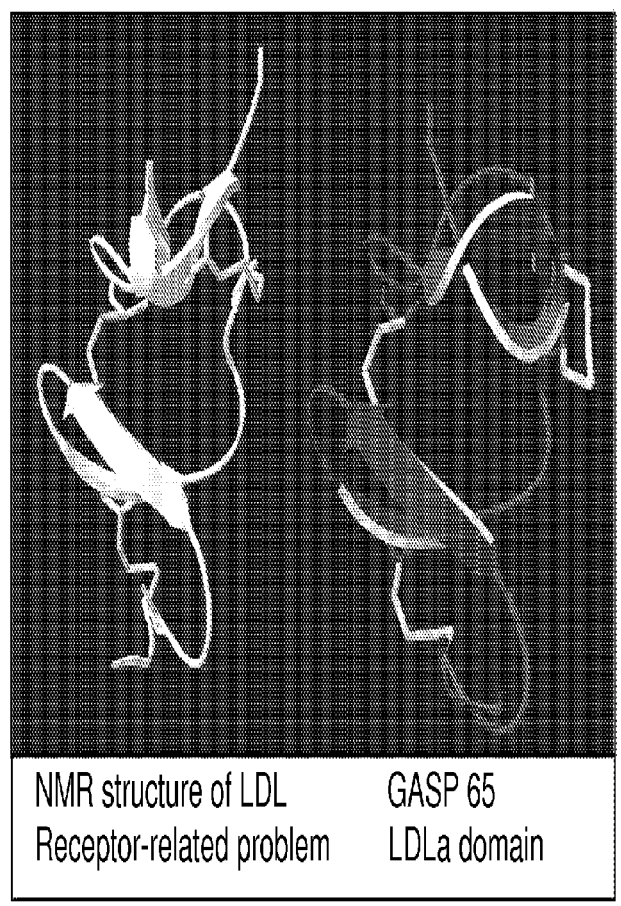

Gastroliths of *Cherax quadricarinatus* were prepared as described [WO 2005/115414]. SDS-PAGE separation of soluble proteins from late premolt gastroliths revealed the presence of at least 6 prominent distinct proteins (FIG. 1A left) with the most abundant being at the size of approximately 65 kDa (gastrolith protein 65, GAP65). Further purification of GAP65 from the entire gastrolith soluble proteins content was performed using DEAE chromatography HPLC with NaCl gradient of up to 1M. GAP65 elution began at 300 mM NaCl but continued mainly at 600 mM (fraction 17). The GAP65 enriched fraction 17 was analyzed by SDS-PAGE and stained with Coomassie (non specific protein staining), "stains all" (negatively charged protein staining), and "pas" (glycoprotein staining), as shown in FIG. 1A right. These staining suggest that GAP65 is the primary protein in this enriched fraction and it is a negatively charged glycoprotein. Trypsin digestion of GAP65 followed by separation using nanospray Qtof2 and sequencing of the peptides using MS-MS generated 7 predicted peptide sequences (FIG. 1B, denoted as SEQ ID NOs. 2-8) which were used for the construction of degenerative primers for the acquisition of a complete GAP65 encoded gene sequence based on gastrolith epithelial disc mRNA. FIG. 2A demonstrates the deduced amino acid sequence of GAP65 open reading frame (also denoted by SEQ ID NO. 1) showing a predicted signal sequence of the N-terminus of the protein (bold). Approximately 4.6% of total amino acids of GAP65 were predicted as possible phosphorylation sites (grey boxes), whereas only three predicted N-glycosylation sites (light boxes including three letters), and two predicted O-glycosylation sites (dark boxes at amino acids no. 72 and 173) were found. The negative charge originates in part from the acidic residues aspartic and glutamic acids, which comprise about 12 mol % of the protein. Bioinformatic analysis of GAP65 sequence suggested, the presence of three known domains (FIG. 2B): chitin binding domain 2 (ChtBD2) from amino acids 29-102 (also denoted by SEQ ID NO. 30), low-density lipoprotein receptor domain class A (LDLa) from amino acids 122-159 (also denoted by SEQ ID NO. 31), and polysaccharide deacetylase domain from amino acids 195-332 (also denoted by SEQ ID NO. 32). FIG. 2C reveals the predicted 3D structure of the LDLa domain based on the homology to NMR structure of complement-like repeat CR3 from the low density lipoprotein receptor-related protein. This LDLa domain is the only known domain in GAP65 which has a predicted calcium binding property.

Example 2

Figure 3B:
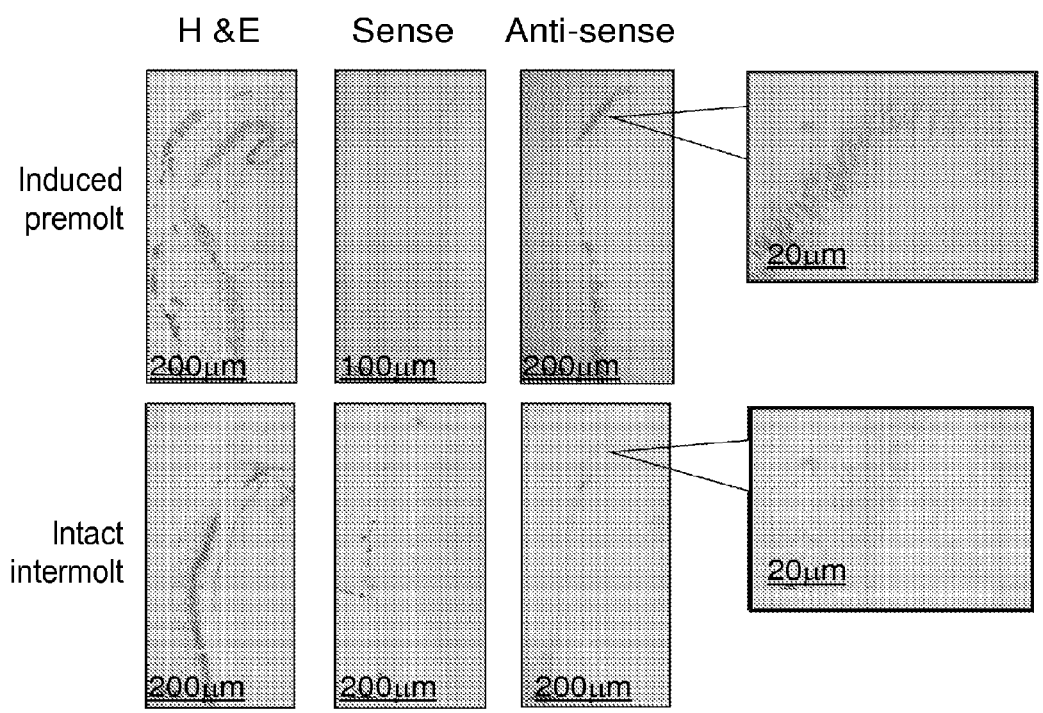

Specific expression of GAP65 was tested in premolt crayfish in several target tissues by means of RT-PCR (FIG. 3A). The expression of GAP65 was detected in the gastrolith epithelial disc and in the sub-epidermal tissue, both are cuticle related tissues. Expression of GAP65 was not detected in the hepatopancreas, stomach wall, and sperm duct. Localization of GAP65 expression in the gastrolith disc of induced premolt and intact intermnolt crayfish by in situ hybridization is presented in FIG. 3B. Left panel represents hematoxylin and eosin staining of the gastrolith disc, middle panel is the control sense probe where no expression is detected. The two right panels represent the anti-sense probe with the last being an enlargement of a specific area. The anti-sense probe reveals that the expression of GAP65 can be detected only in the columnar epithelial cells of the gastrolith disc of an induced crayfish, whereas, in intact intermolt crayfish this expression was not detected.

Example 8

Relative GAP65 transcript levels in the gastrolith epithelial disc following silencing using GAP65 dsRNA were measured using realtime RT-PCR and presented in FIG. 4. GAP65 levels were evaluated in crayfish injected with ecdysone and GAP65 dsRNA, ecdysone and dsRNA carrier, ecdysone and *C. quadricarinatus* vitellogenin (CqVg) dsRNA, and a control injected with both carriers. CqVg an hepatopancreatic specific gene found mostly in reproductive females, served as a control for sequence specific silencing. Transcript levels of crayfish injected with ecdysone and GAP65 daRNA were significantly lower than the levels found in the ecdysone and daRNA carrier injected. In the crayfish injected with ecdysone and CqVg dsRNA, GAP65 transcript levels were similar to the levels detected in the ecdysone and dsRNA carrier injected group. In the control carriers injected crayfish GAP65 transcript levels were higher than the levels found in the ecdysone and GAP65 dsRNA injected crayfish but lower than the levels detected in both the ecdysone and dsRNA injected, and the ecdysone CqVg dsRNA injected crayfish. However, the control carriers group was not statistically significantly different from the three other groups.

Example 4

In order to test the role of GAP65 in gastrolith formation, an RNAi (RNA interference) technique using in vivo injections of GAP65 dsRNA to intermolt crayfish was applied. The initiation of gastrolith formation was achieved by injection of ecdysone. In FIG. 5 gastrolith of crayfish injected with either ecdysone+GAP65 dsRNA, ecdysone+dsRNA carrier, or with carriers of both ecdysone and dsRNA can be seen. FIG. 5A is a lateral view of a representative gastrolith dissected from each treatment group. From this image morphological deformities of the gastrolith can be observed in crayfish injected with both GAP65 dsRNA and ecdysone, whereas in crayfish injected with only ecdysone and dsRNA carrier, the gastrolith appeared normal with no deformities. In the control carriers injected the gastrolith appeared undeveloped or in an initial growth stage. FIG. 5B depicts dorsal X-ray view of the crayfish and gastrolith prior to dissection whereas FIG. 5C presents more contrast images of the images of panel B. In crayfish injected with both GAP65 dsRNA and ecdysone, some regions in which less dense detection of mineral is recoded while the gastrolith disc shape structure was retained. In the ecdysone+dsRNA carrier injected crayfish, the gastrolith appeared normal with no effects on mineral densities. The control carrier gastrolith was too small to be detected by the X-ray imaging.

Example 5

Figures 6A, 6B, 6C:
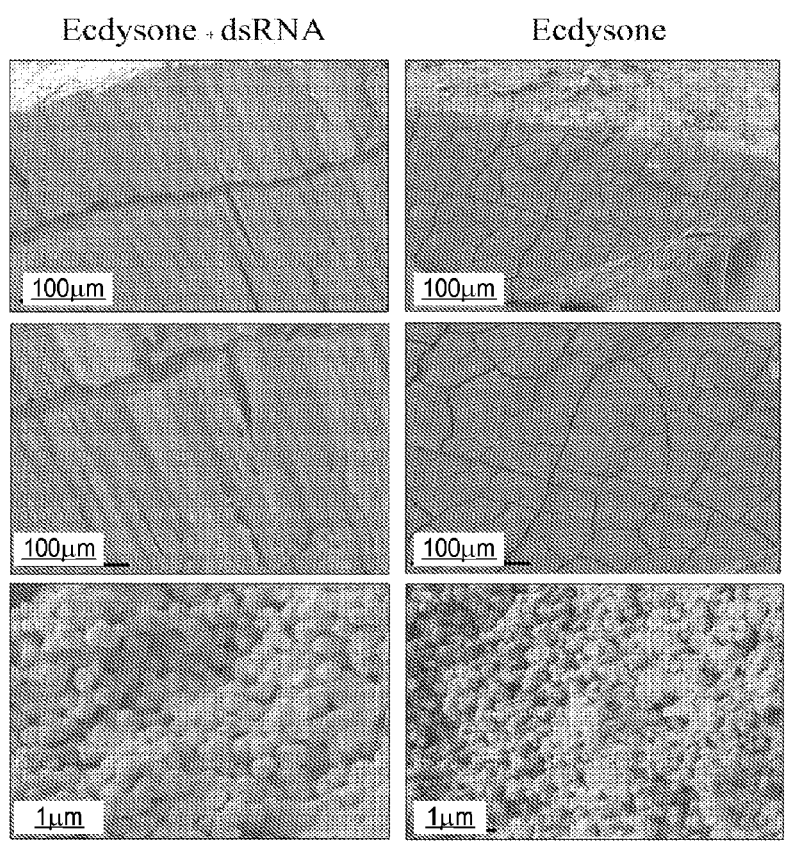
FIGS. 6A-C. show scanning electron microscope (SEM) micrographs of gastroliths structural deformities following GAP65 gene silencing; representative gastroliths were dissected from crayfish injected with ecdysone GAP65 daRNA (left) and ecdysone+dsRNA carrier (right)

Scanning electron microscope (SEM) images of gastroliths dissected from crayfish injected with GAP65 dsRNA and ecdysone, and from crayfish injected only with ecdysone and dsRNA carrier, are presented in FIG. 6. FIG. 6A-B depict images of a cross section through the central part of the gastrolith. In gastrolith of crayfish injected with GAP65 dsRNA and ecdysone severe structural abnormalities can be observed when compared with the gastrolith of ecdysone and dsRNA carrier only injected crayfish. The dense mineral layered structure observed in the gastrolith of ecdysone and carrier injected is replaced with a loosely packed columnar mineralization structure, which resembles hollow straws, in the gastrolith of ecdysone and GAP65 dsRNA injected crayfish. The packaging of the ACC in spherules, and the spherules size, is important for the dense packaging of the gastrolith. ×15000 magnification comparing the spherules size between the two treatments is presented in FIG. 6G. In the less densely arranged gastrolith of crayfish injected with ecdysone and GAP65 dsRNA spherule size ranged between approximately 100-300 nm whereas in the normal ACC deposited in gastrolith of crayfish injected with ecdysone and dsRNA carrier the spherules have narrower size distribution, ranged from 40-60 nm.

Example 6

In order to elucidate the role of GAP65 in the biomineralization process, an in vitro calcium carbonate precipitation essay testing the stabilization of ACC was established. FIG. 7 presents precipitation results of calcium carbonate in the presence of GAP65 and in the presence of other protein (trypsin). SEM images in FIG. 7A indicate the distinct polymorph of calcium carbonate in each treatment. Precipitation of calcium carbonate in the presence of GAP65 resulted in the deposition of an amorphous form (ACC), observed as a thin layer comprised of 100-500 nm spherules. Precipitating experiments performed under the same conditions but in the presence of trypsin resulted with rapid crystallization, observed as large 10 μm single crystals of calcite and vaterite spherulites. FIG. 7B confirms the nature of the ACC in calcium carbonate precipitated in the presence of GAP65. Raman analysis is showing the distinct spectra of ACC with a clear broad peak at 1070 cm$^{-1}$. The presence of GAP65 in the ACC spherules formed by the in vitro precipitation was confirmed by purification of the protein from the mineral fraction of the precipitate and its evaluation by SDS-PAGE against the original GAP65 enriched fraction.

Example 7

Figure 8A:
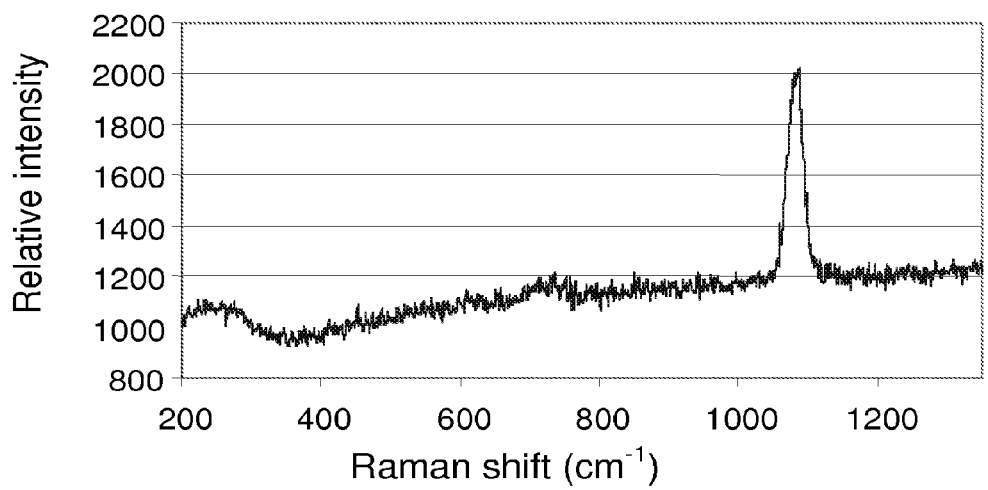
FIGS. 8A-B. shows Raman spectra of the ACC obtained by precipitation with GAP65 enriched fraction.
Figure 8B:
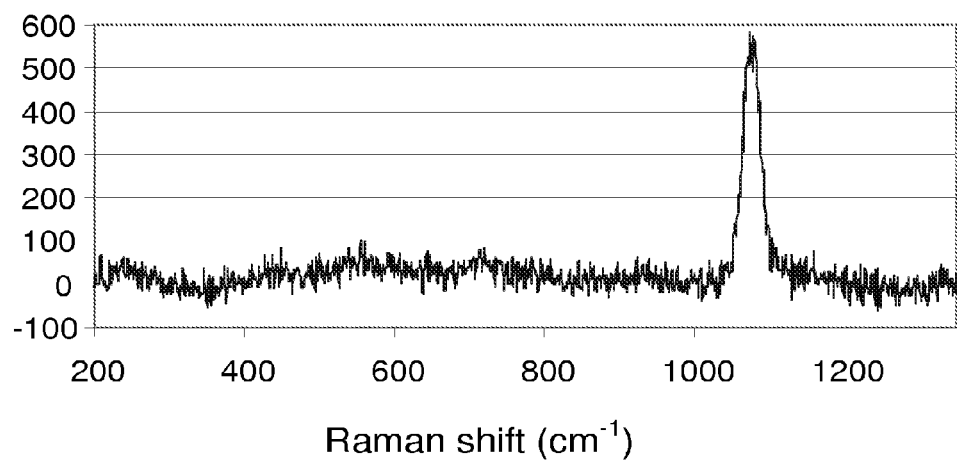
Figure 9A:
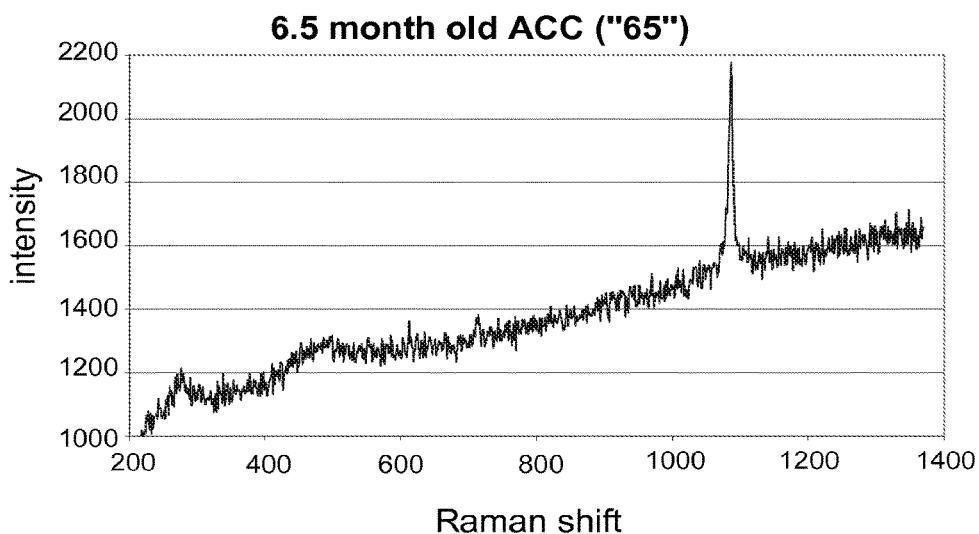
FIGS. 9A-B. are a comparison of the Raman spectra (around the 1085 peak) of 6.5-month old ACC (induced by GAP65) with calcite.
Figure 9B:
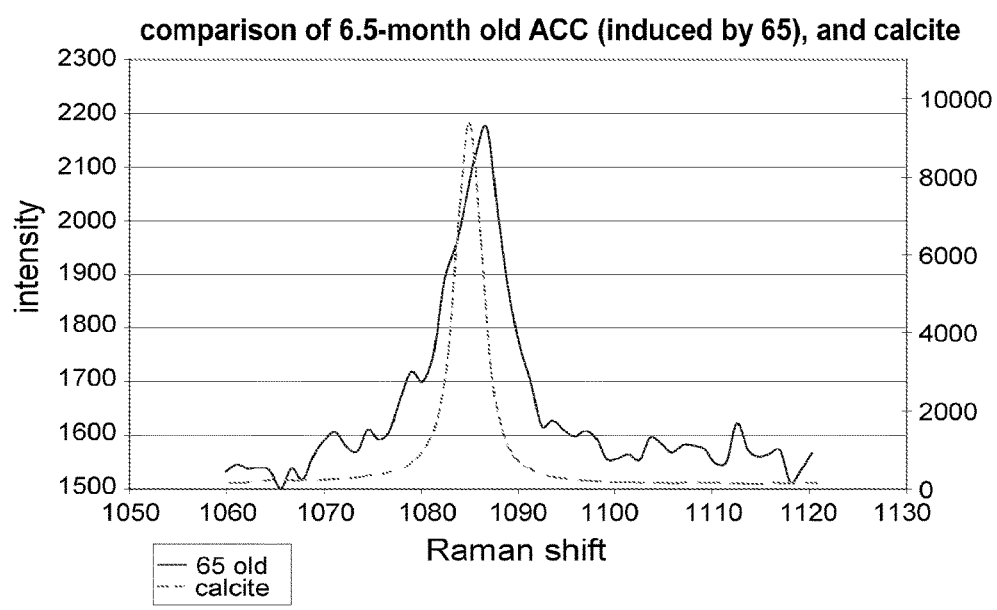
Figure 10A:
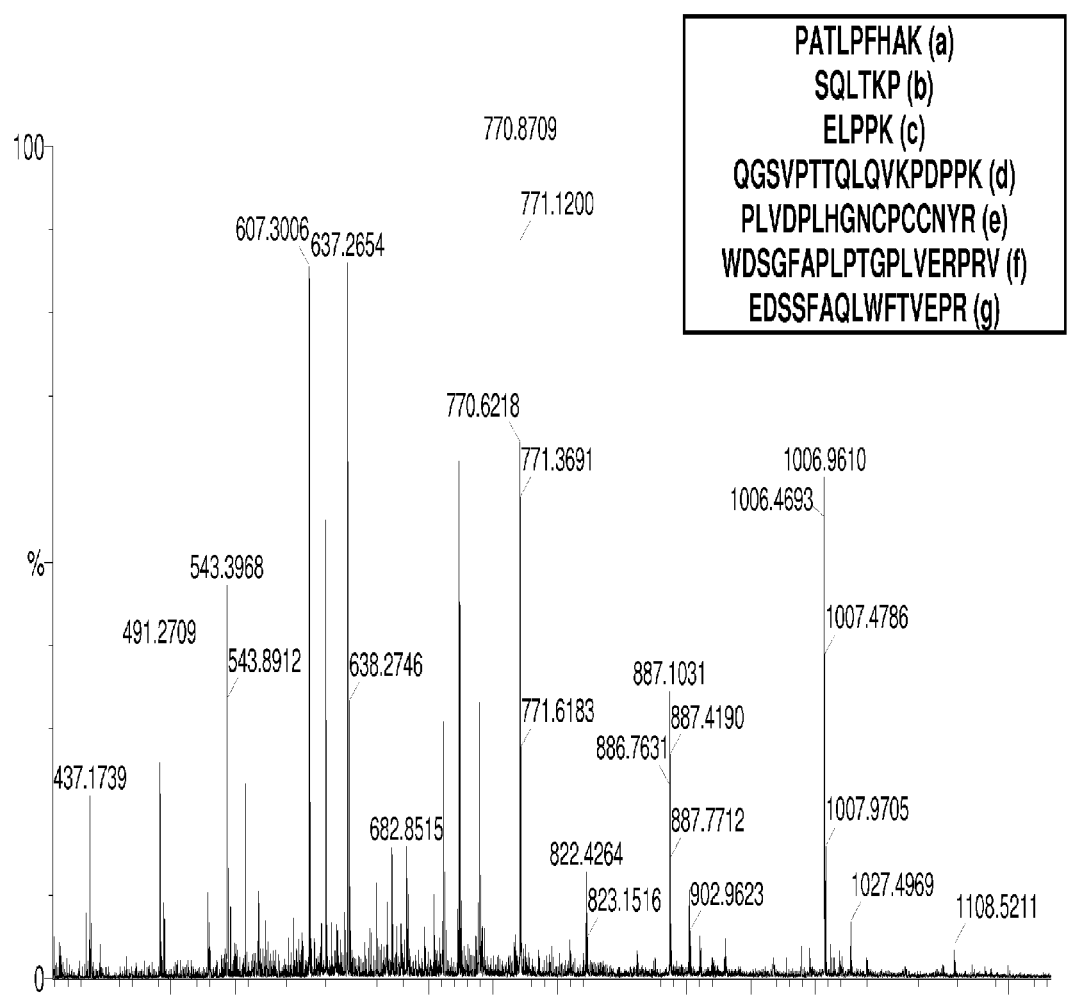
FIGS. 10A-C. show partial sequencing of gastrolith proteins, presented are chromatograms obtained by nanospray Qtof2 following trypsin digestion, sequences of the peptides from significant peaks were obtained through MS/MS analysis.
Figure 10B:
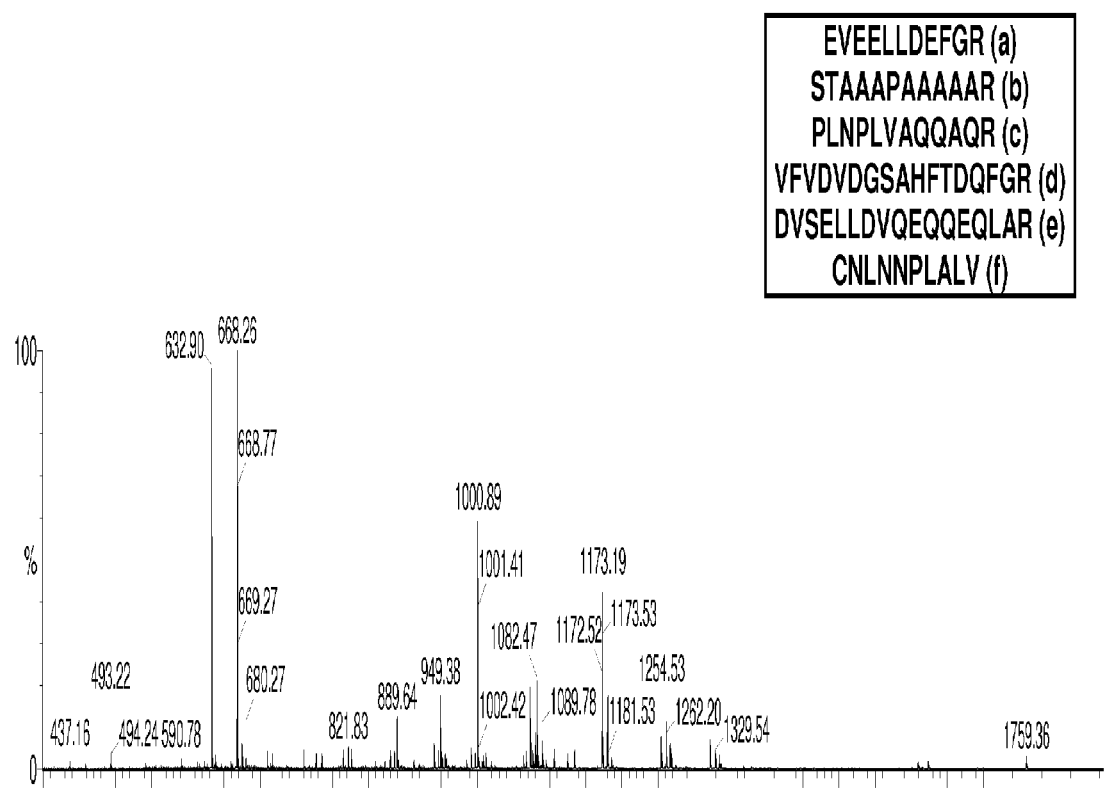
Figure 10C:
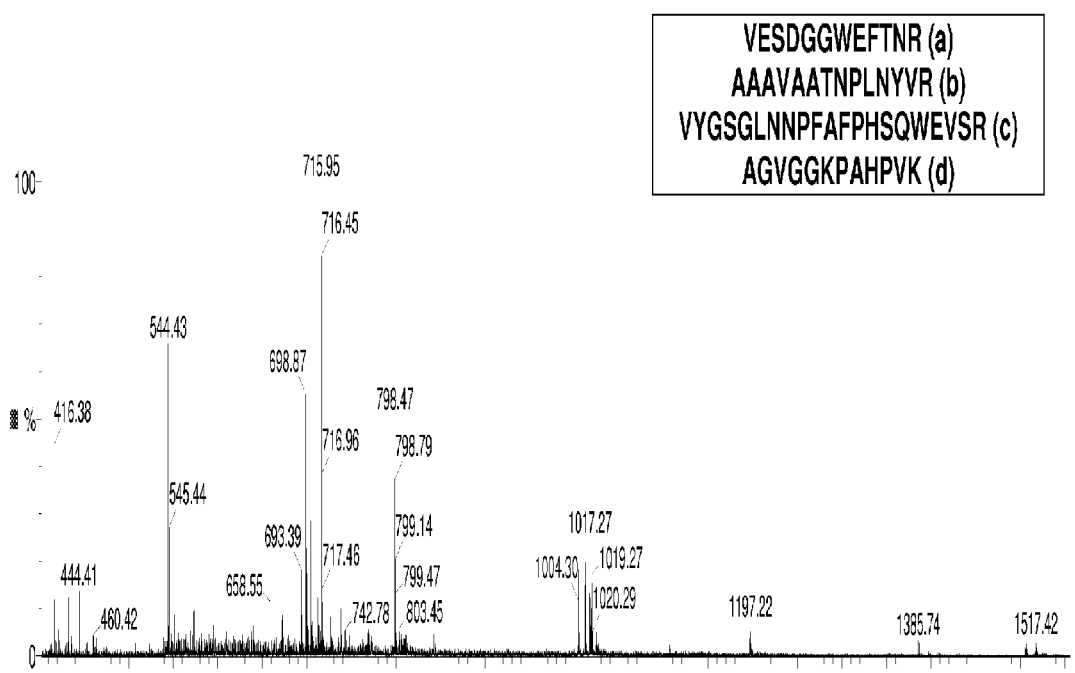

The stability of ACC precipitated with GAP65 was tested by Raman spectroscopy in the samples held at room temperature. 100 μl of 1M $CaCl_2$ was added to 10 ml double distilled water (final concentration: 10 mM). 80 μl from the protein extraction solution (1.2 μg/μl) were added (final concentration ~10 μg/ml), 100 μl of 1M $Na_2CO_3$ (final concentration: 10 mM) was added following an intensive shaking. The vial was centrifuged for 5 min at 4000 rpm, the precipitate was smeared over a glass slide and instantly dried with air flow. The $CaCO_3$ deposits were initially characterized by polarized microscope as a mixture of calcite, vaterite, and ACC. The observations were confirmed by Raman spectroscopy. The ACC was in a form of a thin "crust", and it was estimated to comprise about at least 50% of the total $CaCO_3$. The ACC remained stable at room temperature for at least 1 months, as Raman spectra of the ACC one day after precipitation, 27 days after precipitation, and 6.5 month after precipitation show (FIG. 8A, 8B, 8C). Comparison of the Raman spectra (around the 1085 peak) of 6.5-month old ACC with calcite (FIG. 9) indicated mixture seemingly comprising ACC and vaterite (when considering a shoulder on the 1085 peak possibly being an onset of peak splitting characterizing vaterite).

Example 8

The gastrolith extract inhibits calcium carbonate crystallization and stabilizes the amorphous form of calcium carbonate (ACC). ACC was detected by Raman spectrometry in a precipitate of $CaCO_3$ prepared from a solution containing $CaCl_2$, $Na_2CO_3$ and the gastrolith extract (FIG. 11). The presence of ACC is validated by the presence of a predominant broad peak at about 1080 cm$^{-1}$. The peak at 560 is attributed to the glass substrate. Expressions of the GAP genes were found to be specific to the gastrolith epithelial disc and sub-epidermal tissue, both are cuticle related tissues. Specific expression of GAP21, GAP22 and GAP65 in several target tissues was checked by means of RT-PCR, similarly as described in Example 2. GAP21 and GAP65 expressions were found in both cuticle related tissues. GAP22 expression was found only in the gastrolith epithelial disc. The cDNA sequences of the corresponding genes were obtained and their deduced proteins were found (FIGS. 13-15 and 39). All four proteins were found to contain signal peptides at their N-terminus (underlined amino acids in FIGS. 13-15 and 39 and bold in FIG. 2). Similarity search against databases of conserved domains revealed that GAP65 contains three conserved domains; Chitin-binding domain 2 (also denoted by SEQ ID NO. 30), Low density lipoprotein receptor domain class A (also denoted by SEQ ID NO. 31) and Polysaccharide deacetylase domain (also denoted by SEQ ID NO. 32). GAP12 (also indicated as GAP10), GAP21 and GAP22, on the other hand, show no significant similarity to any known domain.

Blast alignment of GAP12 (also indicated herein as GAP10) and GAP21 revealed a 46.3% identity in the deduced amino acid sequences of these proteins (FIG. 15B).

Physico-chemical analysis of the deduced proteins revealed, that the calculated molecular weights of GAPs 12 (also indicated herein as GAP 10), 21 and 65 are smaller than expected, 9.9, 19.5 and 60.8 kDa respectively, while that of GAP22 is higher than expected, 28.6 kDa (Table 1, FIG. 12). GAP12 (OR GAP10), GAP21 and GAP65 have an acidic pI, therefore they are negatively charged at the physiological pH of the gastrolith (near pH 8.5). GAP12 (also indicated as GAP10) and GAP21 have a high percentage of non-polar, aliphatic amino acids (glycine, alanine and valine) and a high percentage of the polar but uncharged amino acid proline (highlighted in gray in Table 1), GAP65 has a high content of acidic amino acids, but no other distinguishable characteristic. GAP22 has a basic pI, therefore it is positively charged at the physiological pH of the gastrolith. Its main characteristics are a high percentage of the polar but uncharged amino acid proline and of the positively charged arginine. According to bioinformatic analysis, GAP 12 and 21 show some similarities in amino acid composition to other proteins known to be involved in calcium precipitation in crustaceans.

Example 9

Figure 16:
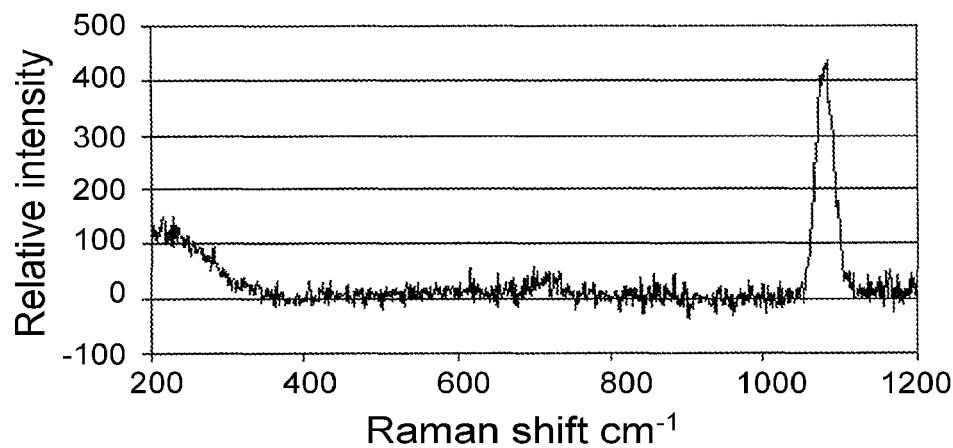
Figure 28:
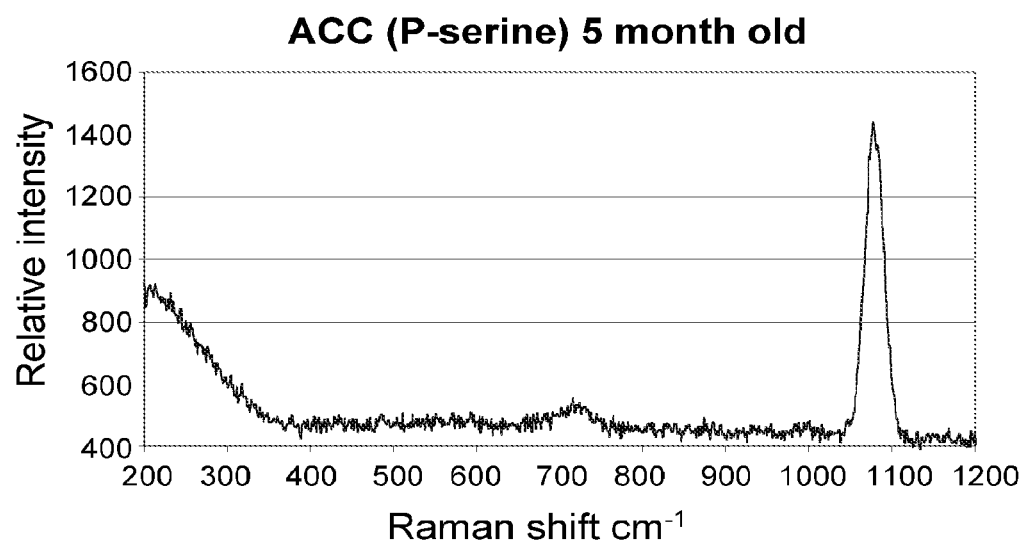
FIG. 28 to FIG. 32 show Raman Spectra of samples prepared according to Examples 9, 10 and 18-20, respectively, which were stored after the precipitation at room temperature as described.

100 μl of 1M $CaCl_2$ were added to 10 ml double-distilled water (DDW), attaining the final concentration of 1.0 mM. 200 μl of P-serine (P-Ser) solution (100 mM) were added to the solution, attaining 2 mM of P-Ser. 100 μl of 1M $Na_2CO_3$ (final concentration: 10 mM) were added following an intensive shaking. The vial was centrifuged for 5 min at 4000 rpm at room temperature. The upper solution was removed and the precipitation was smeared over a glass slide and instantly dried by air flow. RS showed ACC (FIG. 16). The sample was stored at room temperature and tested for ACC stability five months after the precipitation (FIG. 28).

Example 10

Figure 17:
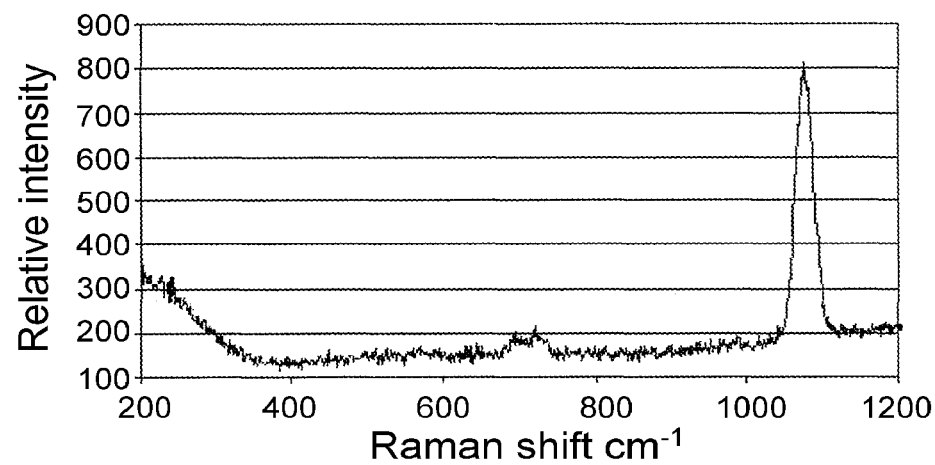
Figure 29:
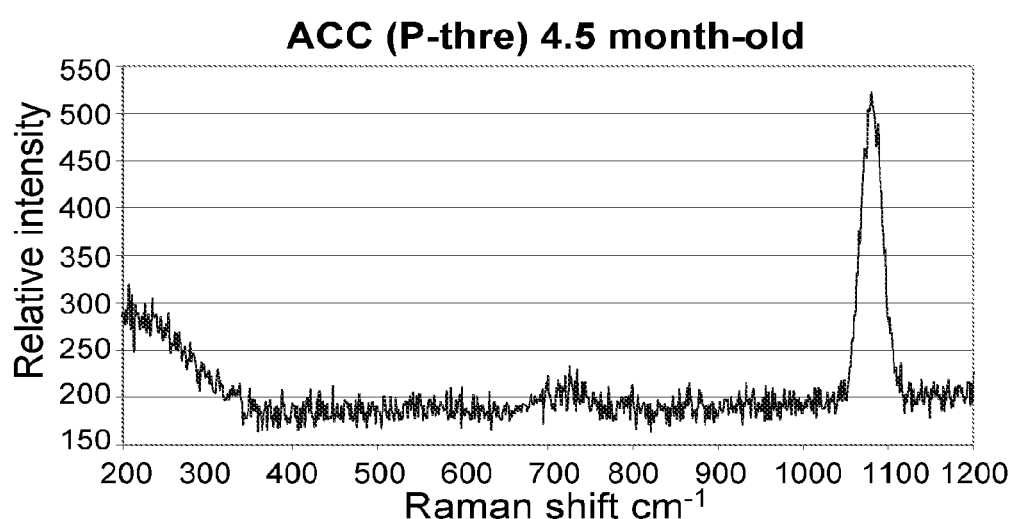

100 µl of 1M $CaCl_2$ were added to 10 ml DDW (final concentration: 10 mM). 100 µl of P-threonine (P-Thr) solution (100 mM) were added to the solution, attaining 1 mM P-Thr. 100 µl of 1M $Na_2CO_3$ (final concentration: 10 mM) were added following an intensive shaking. The vial was centrifuged for 5 min at 4000 rpm at room temperature. The upper solution was removed and the precipitation was smeared over a glass slide and instantly dried by air flow. RS showed ACC (FIG. 17). The sample was stored at room temperature and tested for ACC stability 4.5 months after the precipitation (FIG. 29).

Example 11

Figure 18:
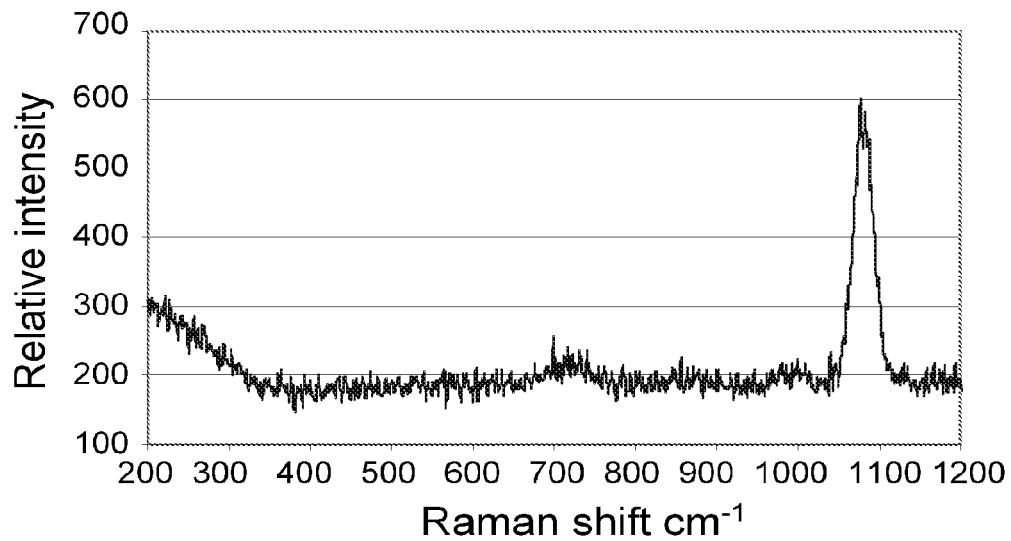

100 µl of 1M $CaCl_2$ were added to 1.0 ml DDW (final concentration: 10 mM). 200 µl of P-serine solution (100 mM) were added to the solution. 100 µl of 1M $Na_2CO_3$ (final concentration: 10 mM) were added following an intensive shaking. The vial was centrifuged for 5 min at 4000 rpm at room temperature. The upper solution was removed and the precipitation was frozen in liquid nitrogen and freeze dried in a lyophilizer. RS showed ACC (FIG. 18).

Example 12

Figure 19:
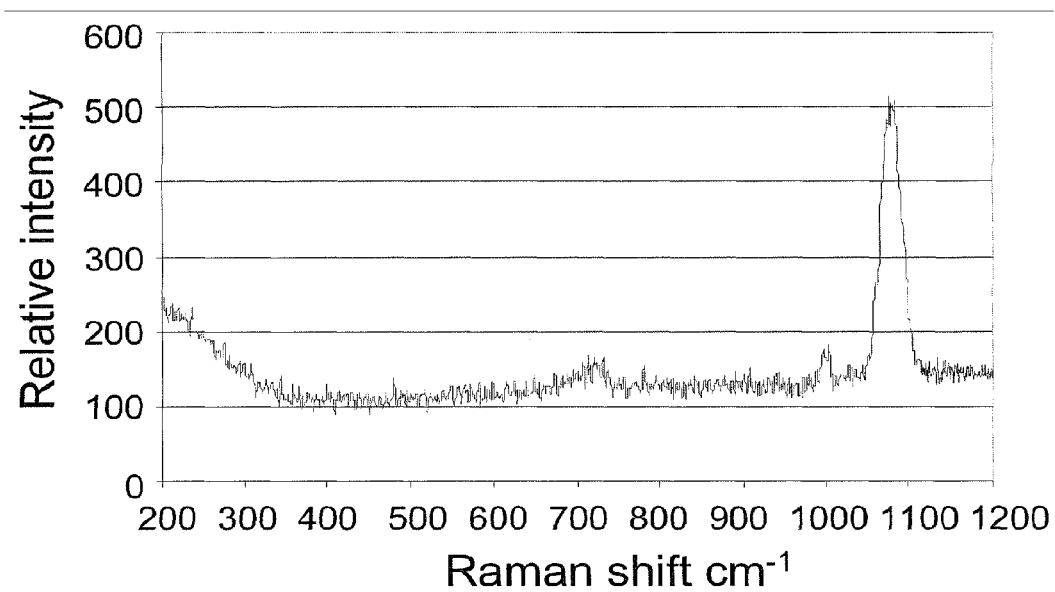

The conditions as described in Example 11 were modified by changing the final concentrations of $CaCl_2$ and $Na_2CO_3$ from 10 mM to 100 mM. RS showed ACC (FIG. 19).

Example 13

Figure 20:
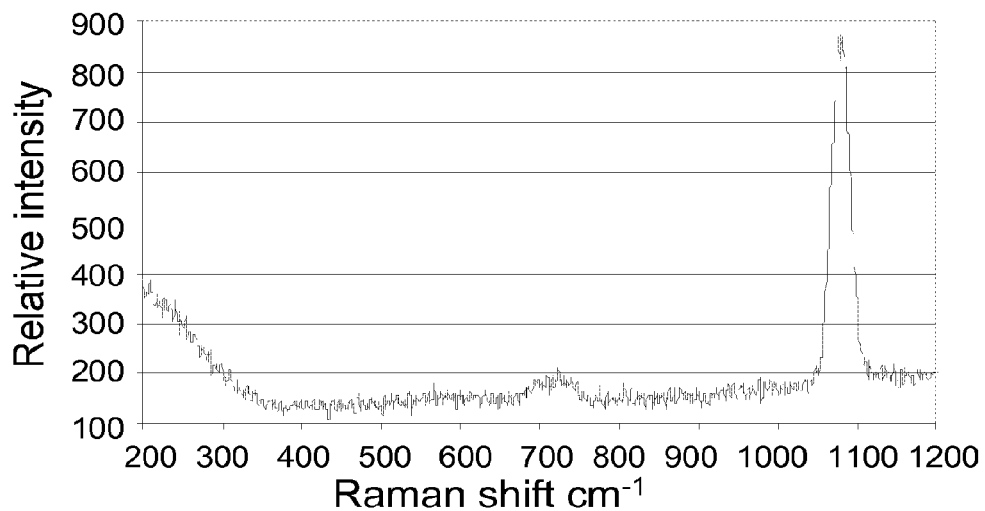

The conditions as described in Example 10 were modified by changing the dehydration method from flowing air to lyophilizing. RS showed ACC (FIG. 20).

Example 14

Figure 21:
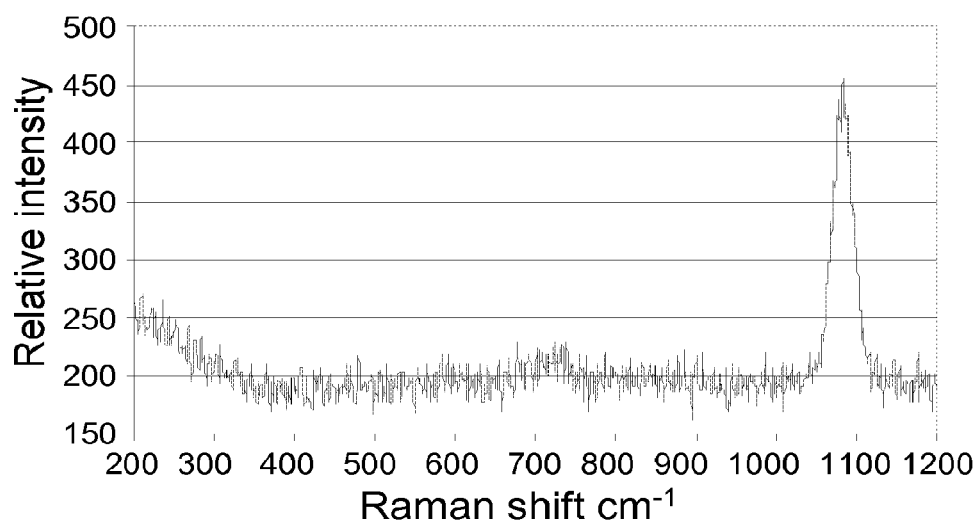

A system comprising 20 mM $CaCl_2$, 20 mM $Na_2CO_3$, 2 mM P-Ser with chitosan (3 wt % Dissolved in 0.2 M acetic acid) that was added to the precipitation solution, after the calcium addition to a final concentration of 0.3 wt %. RS showed ACC (FIG. 21).

Example 15

Figure 22:
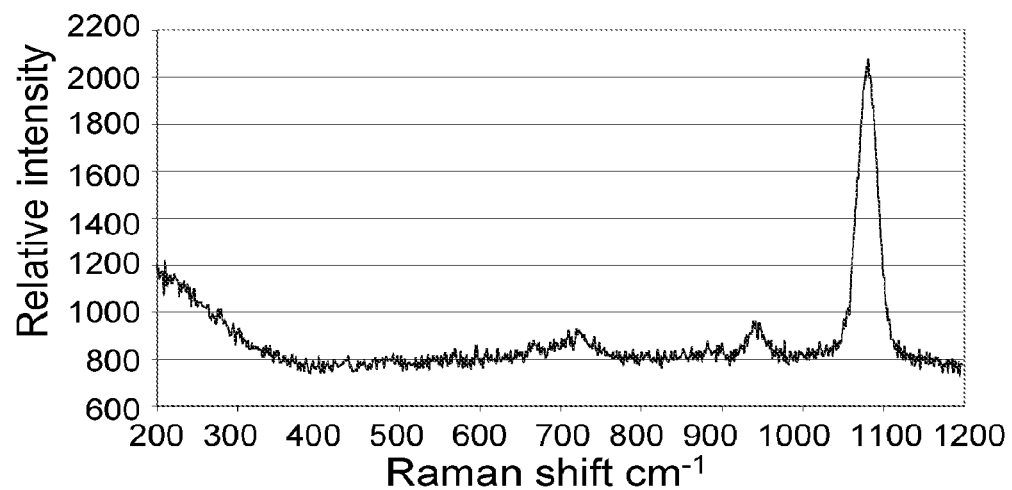

The conditions as described in Example 14 were modified by employing the final concentrations of 0.5 M $CaI_2$, 0.5 M $Na_2CO_3$, and 3 mM P-Ser. This composition represents the upper concentration limit. RS showed ACC (FIG. 22).

Example 16

Figure 23:
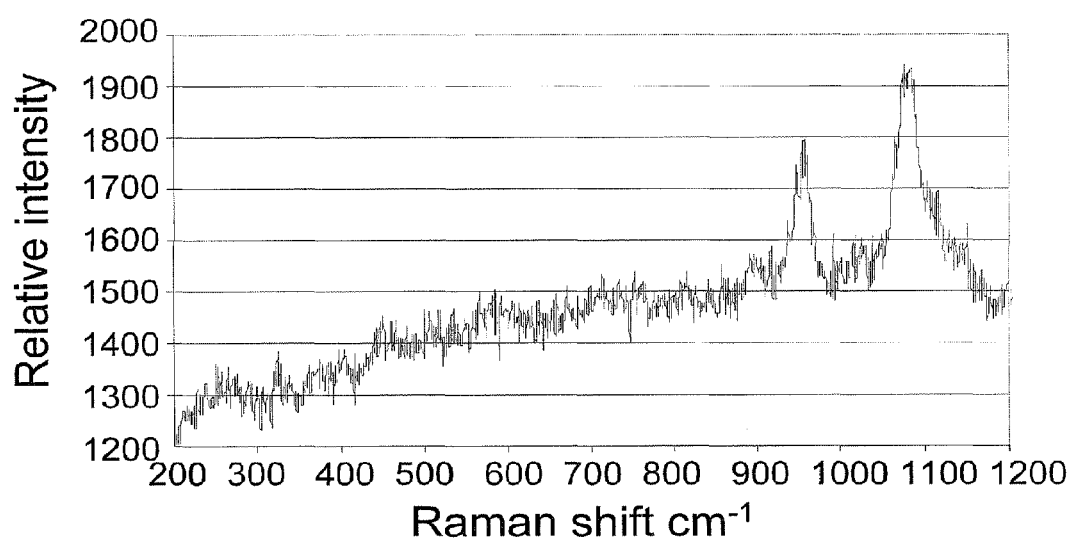

Gastroliths were dissected from endocrinologically-induced premolt crayfish, weighed, rinsed with distilled water and kept at −20° C. After the external layer of the gastrolith was scraped to eliminate any residual external material, the gastroliths were frozen using liquid nitrogen and ground to powder using a mortar and pestle. Demineralization was performed by stirring of each gram of gastrolith powder was in 20 ml of 0.02 M ammonium acetate, 0.5 M EGTA, pH 7.0, on ice. When the $CaCO_3$ dissolution completed, the suspension was centrifuged (2000 rpm, 15-20 min, 4° C.) and the supernatant was collected. The residual insoluble matrix (ISM) was used as additive to the calcifying solution (step ii). 200 µl of the ISM (estimated: ~30 µg protein) were added to 10 ml of the crystallization mixture comprising 10 mM $CaCl_2$ and 10 mM $Na_2CO_3$, followed by air flow dehydration. RS showed ACC (FIG. 23).

Example 17

Figure 24:
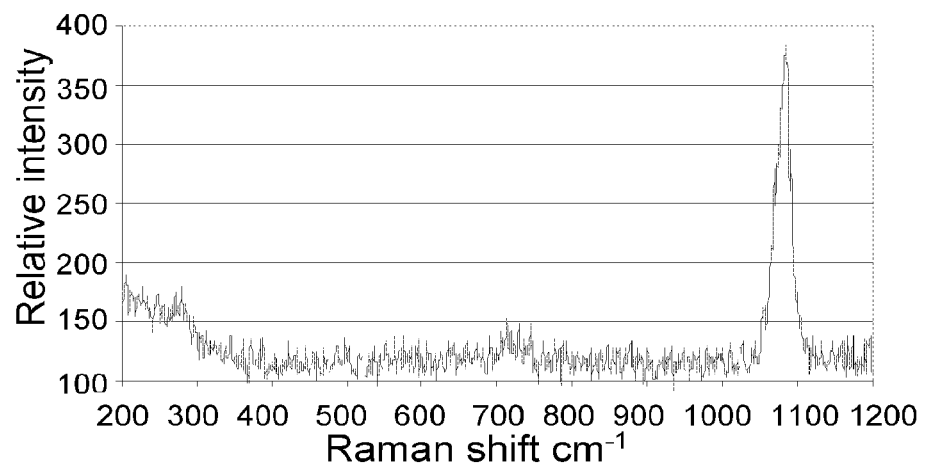

The conditions as described in Example 16 were modified by changing the final concentrations of $CaCl_2$ and $Na_2CO_3$ from 10 mM to 20 mM, and the volume of ISM to 100 µl (~15 µg protein), while dehydrating by means of lyophilizing. RS showed AGO (FIG. 24).

Example 18

Figure 25:
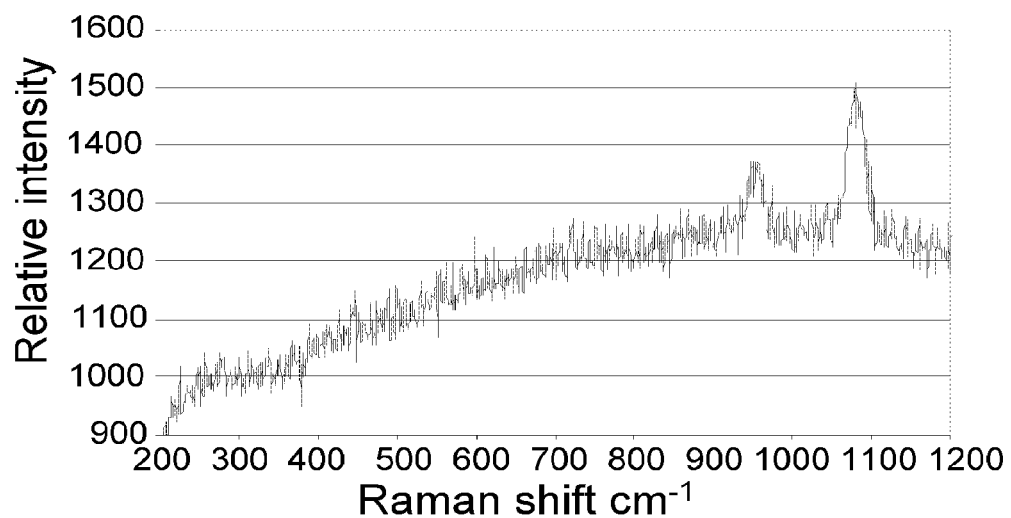

The ISM was treated with various proteolytic enzymes in order to release the chitin binding proteins (either hydrogen or covalent bonding) from the chitinous insoluble phase, and to demonstrate the activity of resulting peptides in ACC induction and stabilization (FIG. 25).

Figure 30:
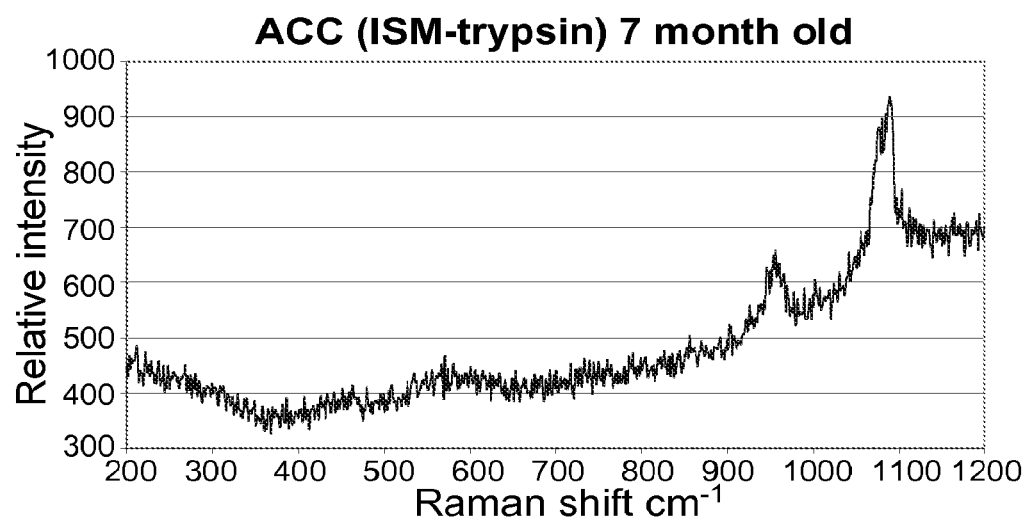

28 ml of ammonium acetate (2 mM) were added to 7 ml of ISM. From this solution 10 ml were mixed with 10 ml of trypsin (3.8 mg/ml) in ammonium acetate (2 mM). The suspensions of the ISM with the proteolytic enzymes were incubated for 2 hr at 4° C. under vortexed condition. After the incubation the vials were centrifuged for 5 minutes at 4000 rpm. The supernatant which contained the ISM digested proteins was removed; 1 ml of the supernatant (equivalent to 100 µl of insoluble matrix and to ~150 µg protein was added to 10 ml of $CaCl_2$ (10 mM). 100 µl of 1M $Na_2CO_3$ (final concentration: 10 mM) were added following an intensive shaking. The vial was centrifuged for 5 min at 4000 RPM, the precipitation was smeared over a glass slide and instantly dried with air flow. RS showed ACC (FIG. 25). The sample was stored at room temperature and tested for ACC stability seven months after the precipitation (FIG. 30).

Example 19

Figure 26:
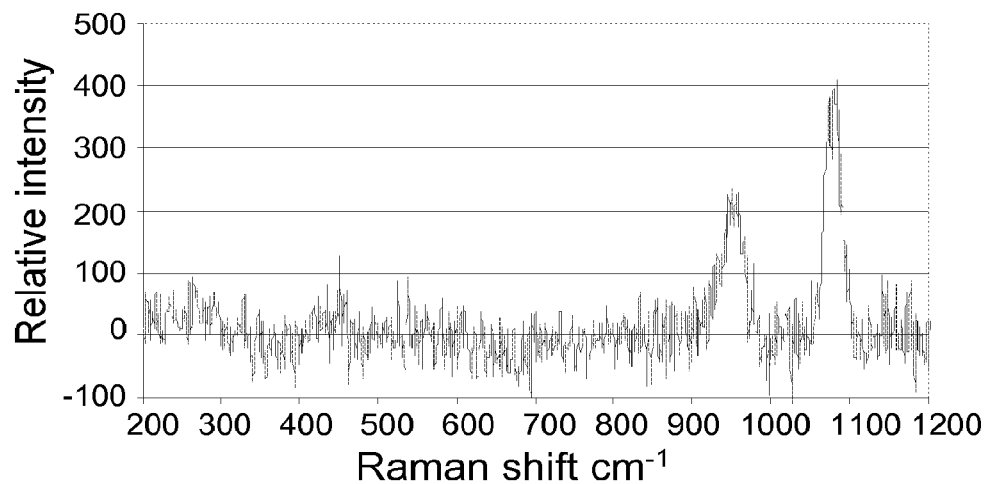
Figure 31:
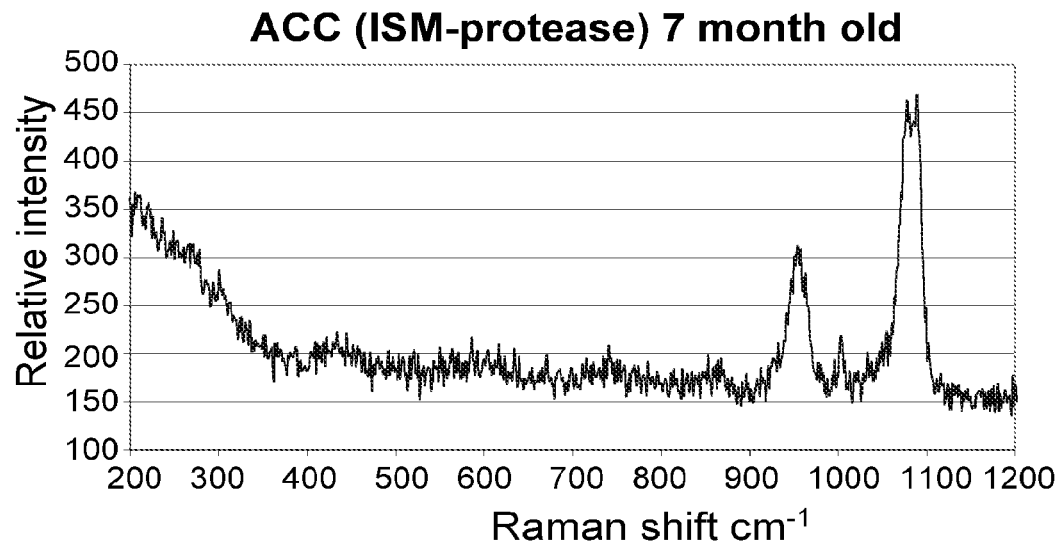

28 ml of ammonium acetate (2 mM) were added to 7 ml of ISM. From this solution 1.0 ml were mixed with 10 ml of protease from *Streptomyces griseus* (Sigma P6911, 0.6 mg/ml) in ammonium acetate (2 mM). The suspensions of the ISM with the proteolytic enzymes were incubated for 2 hr at 4° C. under vortexing. After the incubation the vials were centrifuged for 5 minutes at 4000 rpm. The supernatant which contained the ISM digested proteins was removed; 1 ml of the supernatant was added to 10 ml of $CaCl_2$ (10 mM). 100 µl of 1M $Na_2CO_3$ (final concentration: 10 mM) were added following an intensive shaking. The vial was centrifuged for 5 min at 4000 RPM, the precipitation was smeared over a glass slide and instantly dried with air flow, RS showed the ACC peak (at 1080), and additional secondary peak, possibly of calcium phosphate (peak at 950) (FIG. 26). The sample was stored at room temperature and tested for ACC stability seven months after the precipitation (FIG. 31).

Example 20

Figure 27:
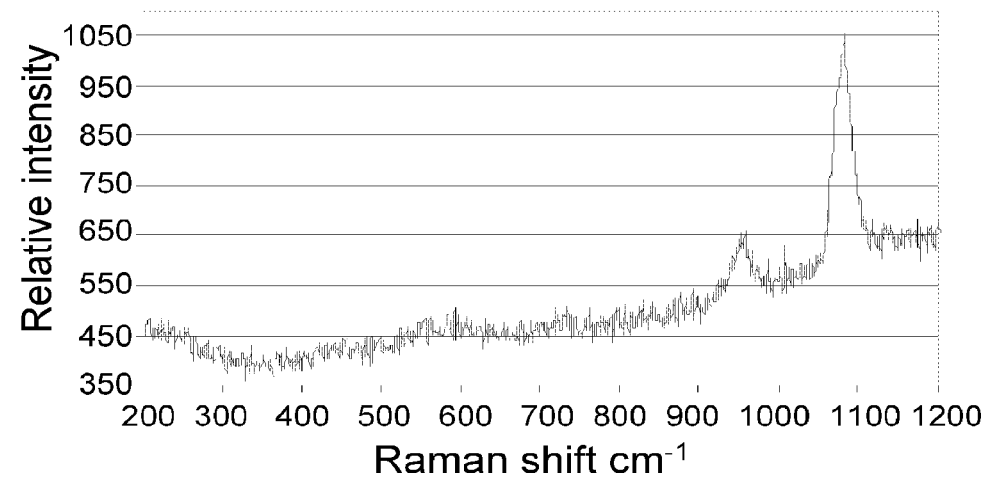
Figure 32:
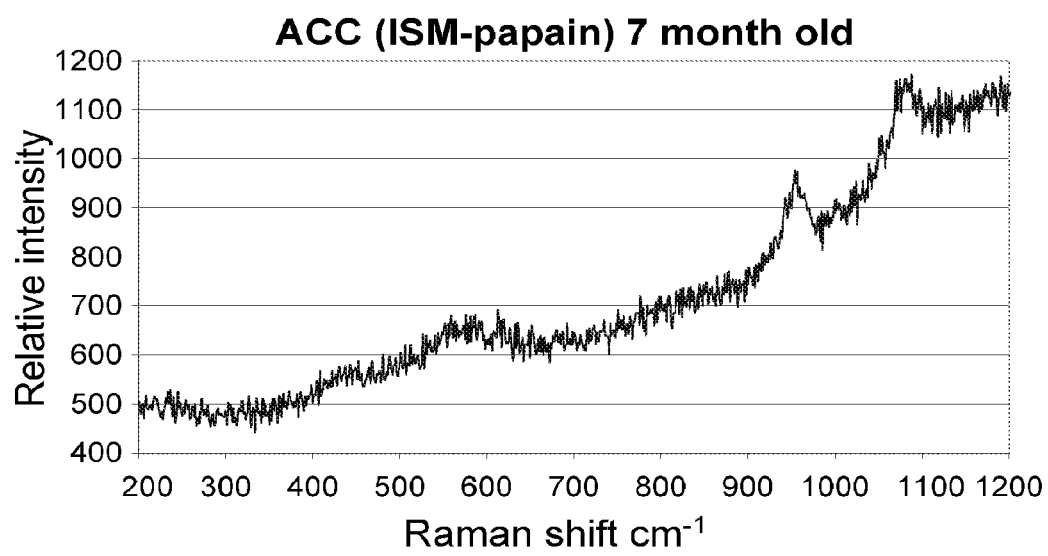

28 ml of ammonium acetate (2 mM) were added to 7 ml of ISM. From this solution 10 ml were mixed with 10 ml of papain (0.26 mg/ml) in ammonium acetate (2 mM). The suspensions of the ISM with the proteolytic enzymes were incubated for 2 hr at 4° C. under vortexed condition. After the incubation the vials were centrifuged for 5 minutes at 4000 rpm. The supernatant which contain now the ISM digested proteins was removed; 1 ml of the supernatant was added to 10 ml of $CaCl_2$ (10 mM). 100 μl of 1M $Na_2CO_3$ (final concentration: 10 mM) were added following an intensive shaking. The vial was centrifuged for 5 min at 4000 RPM, the precipitation was smeared over a glass slide and instantly dried with air flow. RS showed ACC, and possibly calcium phosphate (FIG. 27). The sample was stored at room temperature and tested for ACC stability seven months after the precipitation (FIG. 32).

Example 21

The protein fraction extracted from the gastrolith and eluted from a DEAE column with 100-200 mM NaCl revealed a prominent band, migrating at apparent molecular mass of ~11 kDa. The transcript was successfully sequenced using MS/MS of trypsin-digested fragments, followed by nanospray QT of 2-based degenerative primers, followed by specific primers for 5'- and 3'-rapid amplification of cDNA ends (RACE) (FIG. 39). The 1278-bp transcript comprised a 5' UTR of 53 bp, an ORF of 342 bp encoding a deduced 114 amino acid protein sequence, and a 3' UTR of 880 bp. The first amino acids comprised a signal peptide, with a predicted cleavage site between $Ala^{-1}$ and $Gln^{-1}$. The deduced mature protein has a calculated molecular mass of 10 kDa, and was therefore termed GAP10 (also indicated as GAP12). According to a kinase specific phosphorylation site prediction software, it is suggested that $Ser^{40}$ and $Ser^{74}$ are phosphorylated by Protein kinase A.

GAP10 was not found to be similar to any protein or translated sequence in the GenBank database. However, it does contain two known consensus sequences identified in arthropod cuticular proteins and in spider silk, i.e., one copy of the AAP[A/V] (residues 26-28) repeat and four copies of the glycine-rich GGX (residues 23-25, 32-34, 38-40, 91-93) repeat, and an additional An motif starting at residue 73.

Table 2 (FIG. 38) presents the predicted physicochemical properties of the deduced GAP10 protein (also indicated as GAP12). It has a relatively high percentage (47.5%) of the non-polar aliphatic amino acids, Gly (18%), Ala (15%) and Val (10%), and also of the polar but uncharged amino acids Asn (8%) and Pro (8%). Similar values relating to GAP12 as denoted by SEQ ID NO. 25 are presented by Table 1 in FIG. 12.

Example 22

Figure 33A:
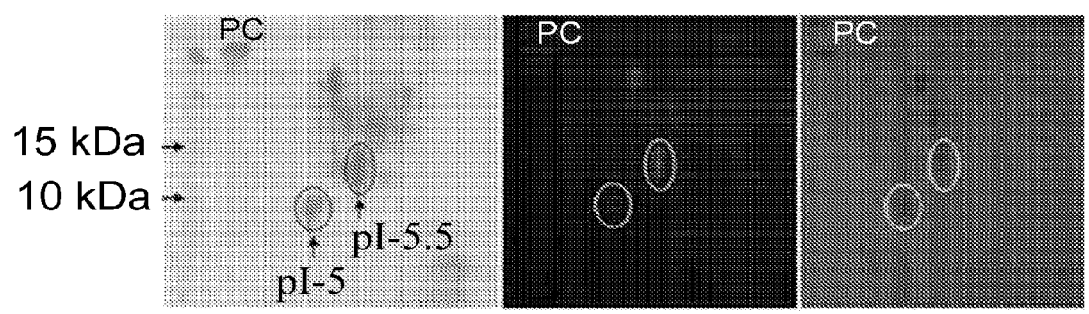
FIGS. 33A-B. relate to the identification of GAP10 and characterization of its phosphorylation and calcium-binding properties.
Figure 33B:
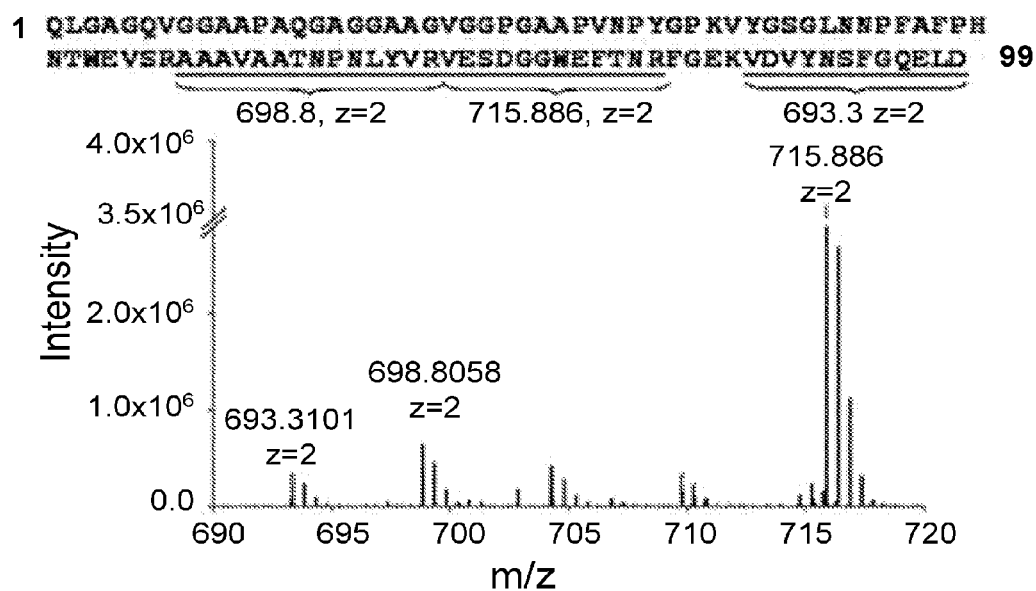

The protein fraction extracted from the gastrolith and that contained GAP10 was separated first by isoelectric focusing and then on SDS-PAGE, revealing several distinct proteins (FIG. 33A, left). A number of these proteins were found to be phosphorylated (FIG. 33A, middle) and to have calcium-binding capacity (FIG. 33A, right). Proteins that were both phosphorylated and calcium-binding were prepared for LC-MS. Two of them, migrating at apparent molecular masses of ~9 and ~11 kDa (circled), were identified as GAP10 (FIG. 33B), and their pIs were calculated as 5 and 5.5, respectively. Since GAP10 has a mildly acidic pI, it is negatively charged at the pH of the gastrolith pouch, which is approximately 8.7.

Example 23

Hybridizations of mRNA from the gastrolith disc of ecdysone-induced promolt animals vs. intermolt control animals to the *C. quadricarinatus* cDNA microarray revealed prominent up-regulation of GAP 10 (also indicated as GAP12) transcripts at premolt (FIG. 34A), GAP10 transcripts (fill circles) were up-regulated up to 65-fold, with an average of approximately 12-fold, and comprised ~12.7% of the total of up-regulated transcripts identified in this experiment.

Figure 34B:
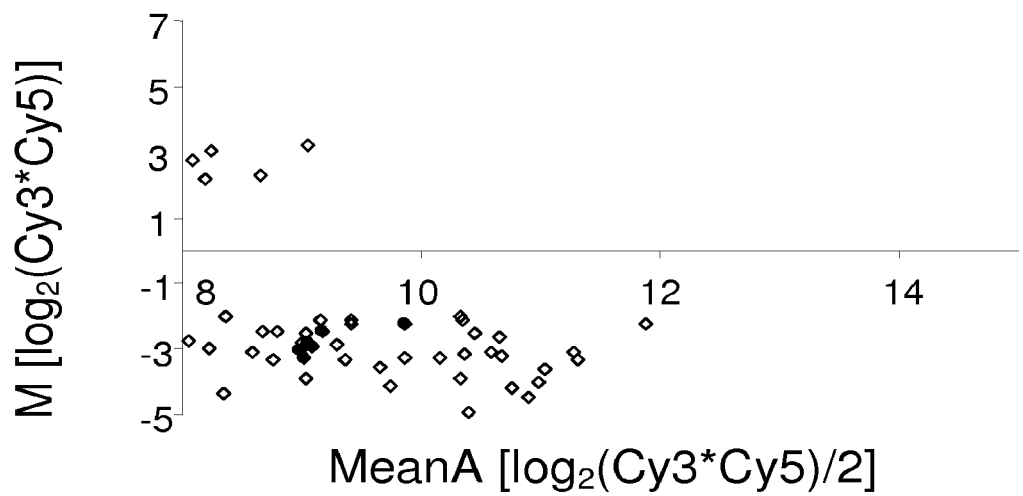
Figure 35A:
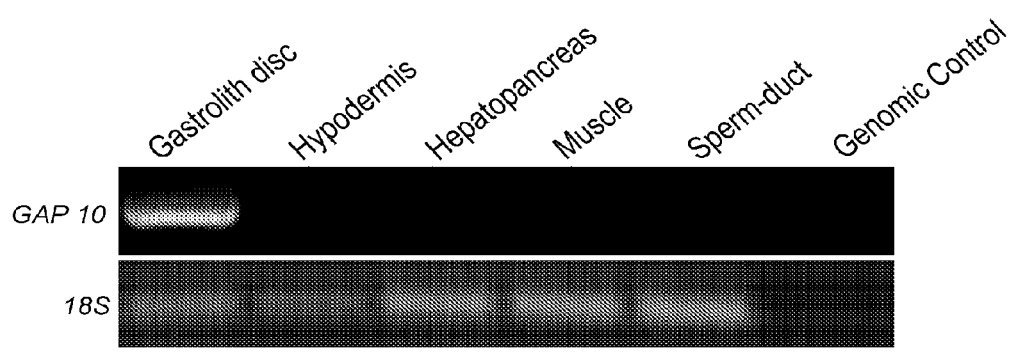
FIGS. 35A-B. show specific expression of GAP 10 in premolt gastrolith disc as demonstrated by RT-PCR (FIG. 35A) and localization of GAP10 expression to the columnar epithelium forming the gastrolith by in situ hybridization (FIG. 35B)
Figure 35B:
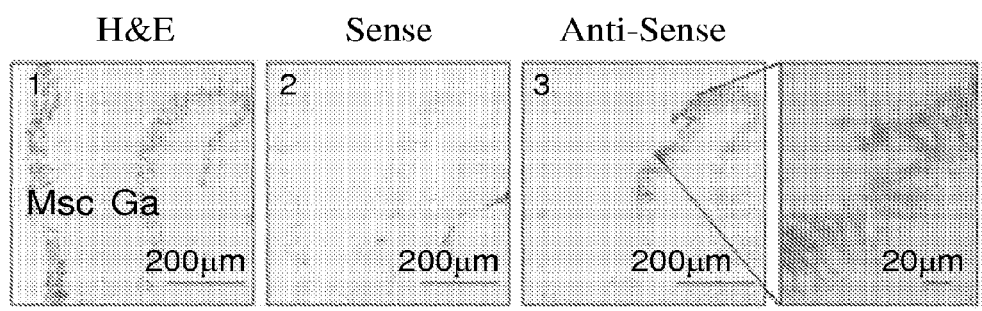

Hybridizations under the same conditions of mRNA from the hypodermal tissue of the same animals at the same molt stages revealed distinct down-regulation of GAP10 transcripts in this tissue, with an average of sevenfold, comprising ~9.2% of the total number of down-regulated transcripts identified in this experiment (FIG. 34B).

Example 24

Specific expression and localization of GAP10 were tested in premolt crayfish in a variety of target tissues by RT-PCR (FIG. 35A) and in situ hybridization (FIG. 35B). Both methods showed expression of GAP10 to be specific to the gastrolith disc during premolt. The transcript, showing a strong, specific signal using an antisense probe, was localized to the columnar epithelium of the gastrolith disc and was not detected in the adjacent muscle tissue (FIG. 35B). No signal was detected with the sense-strand probe.

Example 25

In order to examine the effect of in vivo silencing of GAP10 transcripts during premolt, intermolt males (MMI=0), each weighing 5-10 g were divided to four groups. Ten animals were injected daily with both ecdysone, and dsRNA of GAP 10; eight were injected with ecdysone; six were injected with both ecdysone and dsRNA of CqVg; and four were injected with ecdysone carrier only, i.e., 10% ethanol in Diethyl pyrocarbonate-treated doubly distilled water. Injections were given into the sinus of the first abdominal segment. For each individual crayfish the experiment was terminated at MMI=0.1, at which time the animal was anesthetized and its gastroliths were dissected out. Premolt duration was defined as the number of days until termination. Repeated daily injections of ecdysone together with GAP10 dsRNA to intermolt animals resulted in an increase in premolt duration (the number of days until reaching MMI=0.1) from an average of 10.1 days in the ecdysone-injected control group to 13.1 days in the group receiving ecdysone and GAP10 dsRNA, with the difference between the two groups being significant (P<0.05) (FIG. 36). Another group was injected with ecdysone and CqVg dsRNA (a hepatopancreatic-specific gene found mostly in reproductive females) and served as a control for sequence-specific silencing. The average premolt duration in this group was 8.2 days, which is significantly lower than the value calculated for the ecdysone and GAP10 dsRNA injected group (P<0.05), but not significantly different than the one calculated for the ecdysone-injected control.

Figure 37C:
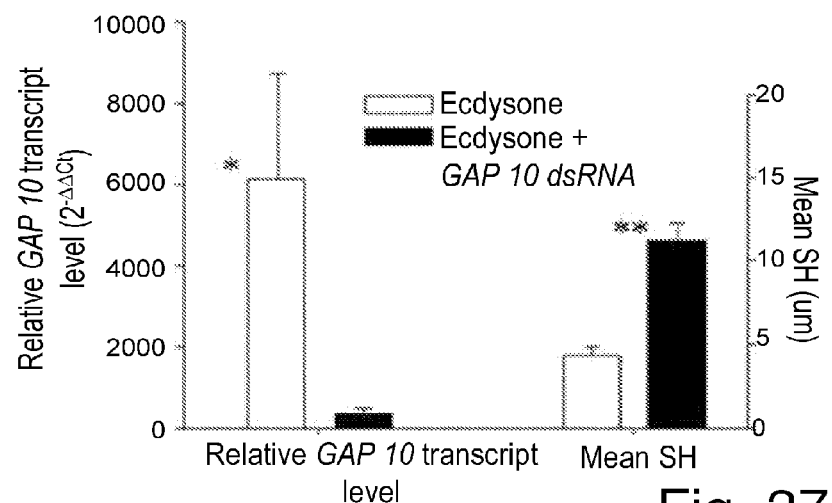

GAP10 silencing resulted in development of gastroliths with significant surface irregularities (FIG. 37A, right) as opposed to the fairly smooth gastroliths that developed in animals injected with ecdysone alone (FIG. 37A, left). For analysis of the gastrolith surface roughness, optical phase interference microscopy (OPIM) analysis was used, providing topographic images of representative surface samples from each group (FIG. 37B). Swedish height (SH) calculations on the topographic images obtained by OPIM revealed a significant difference (P<0.001) between the ecdysone control group (4.4±0.5 μm) and the ecdysone/GAP10 dsRNA-injected group (11.3±1 μm) (FIG. 37C, right). GAP 10 transcript levels in the ecdysone/GAP10 dsRNA-injected group were significantly lower than those found in the ecdysone control group (P<0.01) (FIG. 37C, left).

While this invention has been described in terms of some specific examples, many modifications and variations are possible. It is therefore understood that within the scope of the appended claims, the invention may be realized otherwise than as specifically described.

The invention claimed is:

1. A method of treating a disease or condition comprising administering to a subject in need thereof a pharmaceutical composition consisting of amorphous calcium carbonate (ACC), phosphorylated peptides having amino acid sequence SEQ ID NO:1 or a sequence homologous thereto at least by 90%, and optionally an additional compound selected from the group consisting of: fillers, solvents, and combinations thereof.

2. The method according to claim 1, wherein the disease or condition is selected from the group consisting of bone metabolism disorders, pain, proliferative diseases, neurological disorders, degenerative diseases, immunologic disorders, cardiovascular diseases, pulmonary diseases, nutritional disorders, reproductive disorders, musculoskeletal disorders, and dental problems.

3. The method according to claim 2, wherein the disease or condition is breast carcinoma or bronchogenic carcinoma.

4. The method according to claim 3, wherein said treating comprises slowing down or inhibiting the cell proliferation in a tumor.

5. The method according to claim 1, wherein the disease or condition comprises a bone disorder or a bone marrow disorder.

6. The method according to claim 5, wherein said disorder comprises fracture or osteoporosis.

7. The method according to claim 1, wherein said treating mitigates symptoms of the disease or condition.

8. The method according to claim 1, wherein the disease or condition is pain selected from postoperative pain, pain after injury, pain associated with cancer, and neuropathic pain.

9. The method according to claim 1, wherein the disease or condition is a neurological disorder selected from demyelinating diseases, dementias, and movement disorders.

10. The method according to claim 1, wherein the disease or condition is a degenerative disease selected from multiple sclerosis, Alzheimer's disease, and Parkinson's disease.

11. The method according to claim 1, comprising orally administering the pharmaceutical composition to the subject.

* * * * *